(12) United States Patent
Cataldo et al.

(10) Patent No.: US 8,168,169 B2
(45) Date of Patent: May 1, 2012

(54) METHODS AND COMPOSITIONS FOR THE TREATMENT OF MEDICAL DISORDERS

(75) Inventors: Anne Cataldo, Sutton, MA (US); Chun-Wei Chen, Rochester, NY (US); Bruce M. Cohen, Lexington, MA (US)

(73) Assignee: McLean Hospital Corporation, Belmont, MA (US)

( * ) Notice: Subject to any disclaimer, the term of this patent is extended or adjusted under 35 U.S.C. 154(b) by 1129 days.

(21) Appl. No.: 11/891,138

(22) Filed: Aug. 8, 2007

(65) Prior Publication Data

US 2008/0131409 A1 Jun. 5, 2008

Related U.S. Application Data

(60) Provisional application No. 60/836,513, filed on Aug. 9, 2006.

(51) Int. Cl.
*A61K 48/00* (2006.01)
*C12N 5/0789* (2010.01)
*C12N 5/10* (2006.01)

(52) U.S. Cl. .................. 424/93.21; 435/325; 435/372

(58) Field of Classification Search ............... 424/93.21; 435/325, 372

See application file for complete search history.

(56) References Cited

U.S. PATENT DOCUMENTS

2005/0271639 A1* 12/2005 Penn et al. ............ 424/93.21
2006/0009433 A1* 1/2006 Yao et al. .................. 514/178
2009/0092586 A1* 4/2009 Verfaillie et al. ......... 424/93.7

OTHER PUBLICATIONS

Chen et al. (Jan. 2006) Curr. Alzheimer Res., vol. 3, 63-70.*
Caille et al., "Soluble form of amyloid precursor protein regulates proliferation of progenitors in the adult subventricular zone" Development. May 2004;131(9):2173-2181.
Han et al., "Suppression of cyclin-dependent kinase 5 activation by amyloid precursor protein: a novel excitoprotective mechanism involving modulation of tau phosphorylation" J Neurosci. Dec. 14 2005;25(50):11542-11552.
Ho et al., "The alternatively spliced Kunitz protease inhibitor domain alters amyloid beta protein precursor processing and amyloid beta protein production in cultured cells" J Biol Chem. Nov. 29 1996;271(48):30929-30934.
Mattson et al., "Secreted form of amyloid precursor protein enhances basal glucose and glutamate transport and protects against oxidative impairment of glucose and glutamate transport in synaptosomes by a cyclic GMP-mediated mechanism" J Neurochem. Aug. 1999;73(2):532-537.
Siemes et al., "Keratinocytes from APP/APLP2-deficient mice are impaired in proliferation, adhesion and migration in vitro" Exp Cell Res. Jul. 1, 2006;312(11):1939-1949.
Skovronsky et al., "Protein kinase C-dependent alpha-secretase competes with beta-secretase for cleavage of amyloid-beta precursor protein in the trans-golgi network" J Biol Chem. Jan. 28, 2000;275(4):2568-2575.
Stein et al., "Neutralization of transthyretin reverses the neuroprotective effects of secreted amyloid precursor protein (APP) in APPSW mice resulting in tau phosphorylation and loss of hippocampal neurons: support for the amyloid hypothesis" J Neurosci. Sep. 1, 2004;24(35):7707-7717.
Wang et al., "Secretion of the beta/A4 amyloid precursor protein. Identification of a cleavage site in cultured mammalian cells" J Biol Chem. Sep. 5, 1991;266(25):16960-16964.
Wehner et al., "Cytoprotective function of sAppalpha in human keratinocytes" Eur J Cell Biol. Dec. 2004;83(11-12):701-708.
International Search Report for PCT/US07/17732, dated Aug. 15, 2008.

* cited by examiner

*Primary Examiner* — Anne Marie S Wehbe
(74) *Attorney, Agent, or Firm* — Clark & Elbing, LLP

(57) ABSTRACT

In general, the invention relates to marrow-derived adult progenitor cells (MAPCs) and their use in methods of treating various medical disorders, typically caused by or involving loss of cells or loss of cell function. These cells, when administered, e.g., intranasally, can cross the blood brain barrier and terminally differentiate into cholinergic neurons or otherwise localize and terminally differentiate.

6 Claims, 6 Drawing Sheets
(3 of 6 Drawing Sheet(s) Filed in Color)

METHODS AND COMPOSITIONS FOR THE TREATMENT OF MEDICAL DISORDERS

CROSS-REFERENCE TO RELATED APPLICATIONS

This application claims benefit of U.S. Provisional Application No. 60/836,513, filed Aug. 9, 2006, which is hereby incorporated by reference.

BACKGROUND OF THE INVENTION

The invention relates to methods and reagents for treating neurodegeneration and other medical disorders.

Loss of neurons by a degenerative process is a major pathological feature of many human neurological disorders. Neuronal cell death can occur as a result of a variety of conditions including traumatic injury, ischemia, neurodegenerative diseases (e.g., Parkinson's disease, Huntington's disease, sporadic and familial forms of Alzheimer's disease, Down's syndrome, Frontotemporal dementia, Niemann-Pick's disease, amyotrophic lateral sclerosis (ALS), stroke, or trauma), or as a normal part of tissue development and maintenance. Several inherited disorders produce late onset neuron loss, each of which is highly specific for particular neural cell types. A number of genes have been cloned that are associated with susceptibility to these various neurological disorders (e.g., Huntington's disease, ataxin, and ALS). Epileptic seizures and stroke also produce neurodegeneration in humans and rodents.

Other medical disorders are also caused by abnormal development, cell loss or loss of cell function. This includes psychiatric disorders, such as schizophrenia, schizoaffective disorders, bipolar disorders, and depression.

There is a need for new treatments for these medical disorders.

SUMMARY OF THE INVENTION

In general, the invention features marrow-derived adult progenitor cells (MAPCs) and methods of their use.

In one aspect, the invention features a method for treating a patient having a medical disorder, e.g., of abnormal development, cell loss, or loss of cell function, by administering to the patient MAPCs that either express a trophic factor or have been contacted with a trophic factor prior to administration.

In a related aspect, the invention features a method for treating a patient having a medical disorder, e.g., of abnormal development, cell loss or loss of cell function, by administering to the patient a combination of marrow-derived adult progenitor cells (MAPCs) and a trophic factor.

This invention also provides methods for treating a patient having a medical disorder that can be improved by the presence of cells that express a trophic factor, e.g., a protein, by administering to the patient MAPCs (e.g., recombinant marrow-derived adult progenitor cells) expressing the trophic factor.

For methods of treatment, it will be understood that MAPCs and any trophic factor will be administered in an amount effective to treat the particular disorder. In addition, prior to administering the cells, a patient may be diagnosed as having a particular medical condition to be treated. Administration of MAPCs may occur more than once during a treatment regime. Furthermore, any compounds, e.g., trophic factors, administered with MAPCs during a course of treatment may be administered in the same or different formulations and, in the latter case, either concomitantly and at different times. Additional compounds, e.g., trophic factors, may also be administered at different intervals than MAPCs and for periods after administration of MAPCs has ceased.

In any of these embodiments, the trophic factor expressed in, contacted with, or combined with the cells is desirably selected to promote differentiation into the cells of the type located at the site of disease, e.g., neurons, muscle cells, pancreatic cells, hepatocytes, and hematopoietic lineage cells to promote survival until reaching a site of disease, or to promote cell growth. Exemplary trophic factors include sAPPα (e.g., human, chimpanzee, orangutan, macaque, mouse, and rat sAPPα) and trophic factors selected from Table 1.

A preferred route of administration is intranasal.

The cells employed in the methods of the invention may be autologous (i.e., obtained from the patient treated), allogeneic (i.e., from the same species as the patient), or xenogeneic (i.e., from a species different from that of the patient).

The above methods of treatment can be used to treat a medical disorder capable of being treating by replacement of lost cells or lost cell function. Loss of cells includes conditions in which cells are destroyed by physical injury, chemical toxicity, or biological mechanisms, e.g., loss of neurons in Alzheimer's disease. Loss of function includes conditions where cells may be present but are not producing the desired biological effect or cells are present and produce an effect that inhibits an otherwise desirable biological effect. Medical conditions include, for example, a neurodegenerative disease (e.g., Alzheimer disease, Down's syndrome, Frontotemporal dementia, Niemann-Pick's disease, Parkinson's disease, Huntington's disease (HD), dentatorubropallidoluysian atrophy, Kennedy's disease, spinocerebellar ataxia, fragile X syndrome, fragile XE mental retardation, Friedreich's ataxia, myotonic dystrophy, spinocerebellar ataxia type 8, spinocerebellar ataxia type 12, Alexander disease, Alper's disease, amyotrophic lateral sclerosis, ataxia telangiectasia, Batten disease, Canavan disease, Cockayne syndrome, corticobasal degeneration, Creutzfeldt-Jakob disease, ischemia stroke, Krabbe disease, Lewy body dementia, multiple sclerosis, multiple system atrophy, Pelizaeus-Merzbacher disease, Pick's disease, primary lateral sclerosis, Refsum's disease, Sandhoff disease, Schilder's disease, spinal cord injury, spinal muscular atrophy, Steele-Richardson-Olszewski disease, and Tabes dorsalis), a psychiatric disorder (e.g., depression, bipolar disorders, schizophrenia, schizoaffective disorder, and anxiety disorders (e.g., panic disorder and post traumatic stress disorder)), an ischemia related disease (e.g., heart attack, myocardial ischemia, stroke, diabetic ischemia, critical limb ischemia, and intestinal ischemia), a degenerative muscle disease (e.g., Duchenne muscular dystrophy, Becker muscular dystrophy, Emery-Dreifuss muscular dystrophy, limb girdle muscular dystrophy, myotonic dystrophy, oculopharyngeal muscular dystrophy, and distal muscular dystrophy), diabetes, or an autoimmune disease.

In another aspect, the invention features a method for the delivery of cells to the central nervous system (CNS), e.g., the brain or spinal column, of a mammal by intranasally administering eukaryotic cells, such as stems cells and MAPCs, so that at least a portion of said cells contact the CNS. In certain embodiments, the cells, e.g., stem cells or MAPCs, cross the blood brain barrier (BBB). As with other methods described herein, the eukaryotic cells, e.g., stem cells or MAPCs, may express a trophic factor (e.g., constitutively, by induction, or recombinantly). The eukaryotic cells, e.g., stem cells or MAPCs, may also be contacted with a trophic factor prior to administration, or the administration may further include a trophic factor.

This invention also features marrow-derived adult progenitor cells expressing recombinant sAPPα, marrow-derived adult progenitor cells contacted with a trophic factor in vitro, and pharmaceutical compositions including the same. In one embodiment, the invention provides a pharmaceutical composition including MAPCs and a pharmaceutically acceptable excipient for intranasal administration. MAPCs may express a trophic factor in any manner described herein, may have been contacted with a trophic factor prior to formulation, or may be formulated with an ex vivo trophic factor.

As is also described herein, the methods of the invention may employ progenitor cells other than MAPCs. Such cells may be differentiated from MAPCs or obtained from a suitable animal, e.g., the patient being treated.

"Marrow-derived adult progenitor cells" or "MAPCs" refer to a population of specialized mesenchymal cells in the adult bone marrow that give rise to mesoderm, endoderm, neuroectoderm, and skin, and exhibit many of the same traits as embryonic stem cells. The term also includes marrow-derived adult progenitor cells that have been contacted with a trophic factor in vitro and to cells passaged from marrow-derived adult progenitor cells.

"Autologous" refers to cells which are isolated from a patient and then administered to the patient from whom they were isolated.

"Treating" and "treatment" refer to reduction in severity, progression, spread, and/or frequency of symptoms, elimination of symptoms and/or underlying cause, prevention of the occurrence of symptoms and/or their underlying cause, and improvement or remediation of damage. "Treatment" is meant to include therapeutic treatment as well as prophylactic, or suppressive measures for the disease or disorder.

By "patient" is meant any animal (e.g., a human). Other animals that can be treated using the methods, compositions, and kits of the invention include horses, dogs, cats, pigs, goats, rabbits, hamsters, monkeys, guinea pigs, rats, mice, lizards, snakes, sheep, cattle, fish, and birds.

"Neurodegenerative disease" refers to diseases of the nervous system (e.g., the central nervous system or peripheral nervous system) characterized by abnormal cell death. Examples of neurodegenerative diseases include Alzheimer disease, Down's syndrome, Frontotemporal dementia, Niemann-Pick's disease, Parkinson's disease, Huntington's disease (HD), dentatorubropallidoluysian atrophy, Kennedy's disease (also referred to as spinobulbar muscular atrophy), and spinocerebellar ataxia (e.g., type 1, type 2, type 3 (also referred to as Machado-Joseph disease), type 6, type 7, and type 17)), fragile X syndrome, fragile XE mental retardation, Friedreich's ataxia, myotonic dystrophy, spinocerebellar ataxia type 8, and spinocerebellar ataxia type 12, Alexander disease, Alper's disease, amyotrophic lateral sclerosis, ataxia telangiectasia, Batten disease (also referred to as Spielmeyer-Vogt-Sjogren-Batten disease), Canavan disease, Cockayne syndrome, corticobasal degeneration, Creutzfeldt-Jakob disease, ischemia stroke, Krabbe disease, Lewy body dementia, multiple sclerosis, multiple system atrophy, Pelizaeus-Merzbacher disease, Pick's disease, primary lateral sclerosis, Refsum's disease, Sandhoff disease, Schilder's disease, spinal cord injury, spinal muscular atrophy, Steele-Richardson-Olszewski disease, and Tabes dorsalis.

"Ischemia related disease" refers to diseases characterized by insufficient blood supply to a tissue or organ and which can result in damage or dysfunction of the tissue or organ (e.g., heart, brain, intestine, liver, kidney, muscle, and eye), and can be due to any number of causes including, for example, vascular occlusion (caused by, e.g., athero-arteriosclerosis, plaque formation or thrombosis) or other injury.

"Trophic factor" is a chemical species that includes at least one of the following characteristics: promotes the lineage specific differentiation of cells, promotes cell growth, and/or promotes survival of endogenous cells in a tissue. For example, a "neurotrophic factor" promotes growth and differentiation of neurons. Exemplary trophic factors are proteins.

"sAPPα" refers to any protein which has the biological activity of the soluble fragment of the amyloid precursor protein when cleaved by alpha-secretase (Esch et al., Science 248:1122 (1990)). This biological activity is characterized by the enhancement of the neuritogenic and neuroprotective activities of NGF in certain neuron types (Mattson, J. Neurobiol. 25:439-450 (1994), Araki et al., Biochem. Biophy. Res. Commun. 181:265-271 (1991)).

The amyloid precursor protein can be from human, mouse, or from any other vertebrate. Examples of sAPPα include human sAPPα (encoded by the nucleic acid sequence set forth in SEQ ID NO:1) and sAPPα xenologues. Examples of sAPPα xenologues are chimpanzee sAPPα, orangutan sAPPα, macaque sAPPα, rat sAPPα, and mouse sAPPα (examples of nucleic acid sequences of sAPPα xenologues are set forth in Sequence Appendix A).

The term "sAPPα" also means any functional sAPPα fragment, or any fusion of functional sAPPα fragments. Furthermore, "sAPPα" embraces fragments having an additional amino terminal methionine.

The term "sAPPα" also means any fusion of sAPPα, or a functional fragment thereof, with another polypeptide. These fusions include, but are not limited to, GST-sAPPα, HA tagged sAPPα, or Flag tagged sAPPα. These additional polypeptides may be linked to the N-terminus and/or C-terminus of sAPPα.

The term "sAPPα" also includes any chimeric sAPPα protein. By "chimeric sAPPα" is meant a protein including a fusion of a sAPPα domain or domains with a portion of sAPPα from a different species, wherein the chimeric sAPPα retains the properties of human sAPPα, e.g., as determined by the enhancement of the neuritogenic and neuroprotective activities of NGF in certain neuron types (Mattson, J. Neurobiol. 25:439-450 (1994), Araki et al., Biochem. Biophy. Res. Commun. 181:265-271 (1991)).

The term "sAPPα" is also meant to include any protein, or a functional fragment thereof, with at least 45%, e.g., at least 60%, 75%, or 90% (e.g., 91%, 92%, 93%, 94%, 95%, 96%, 97%, 98%, or 99%) amino acid sequence identity to the amino acid sequence of human sAPPα (encoded by the human sAPPα nucleic acid sequence set forth in SEQ ID NO:1) or corresponding fragment thereof. The term also includes any conservative substitutions of amino-acid residues in sAPPα. The term "conservative substitution" refers to replacement of an amino acid residue by a chemically similar residue, e.g., a hydrophobic residue for a different hydrophobic residue, a charged residue for a different charged residue, etc. Examples of conserved substitutions for non-polar R groups are alanine, valine, leucine, isoleucine, proline, methionine, phenylalanine, and tryptophan. Examples of substitutions for polar, but uncharged, R groups are glycine, serine, threonine, cysteine, asparagine, or glutamine. Examples of substitutions for negatively charged R groups are aspartic acid or glutamic acid. Examples of substitutions for positively charged R groups are lysine, arginine, or histidine.

The term "identity" is used herein to describe the relationship of the sequence of a particular nucleic acid molecule or polypeptide (or a fragment thereof) to the sequence of a reference molecule of the same type (or a fragment thereof).

For example, if a nucleic acid or amino acid molecule has the same nucleotide or amino acid residue at a given position, as compared to a reference molecule to which it is aligned, there is said to be "identity" at that position. The level of sequence identity of a nucleic acid molecule or a polypeptide to a reference molecule is typically measured using sequence analysis software with the default parameters specified therein, such as the introduction of gaps to achieve an optimal alignment (e.g., Sequence Analysis Software Package of the Genetics Computer Group, University of Wisconsin Biotechnology Center, 1710 University Avenue, Madison, Wis. 53705, BLAST, or PILEUP/PRETTYBOX programs). These software programs match identical or similar sequences by assigning degrees of identity to various substitutions, deletions, or other modifications.

The appeal of MAPCs for clinical use is due to fewer ethical concerns than embryonic stem cells (ESCs) and their ability to easily expand, differentiate into a variety of tissues, and, in particular, cross the BBB moving into regions that undergo neurodegeneration. Because these cells can be derived from the patient, they provide an autologous transplantation strategy reducing the need for immunosuppression and suggest that the adult bone marrow can provide an additional source of neural cells.

Other features and advantages will be apparent from the following description and the claims.

BRIEF DESCRIPTION OF THE DRAWINGS

The application file contains drawings executed in color (FIGS. 1, 2, and 5). Copies of this patent or patent application with color drawings will be provided by the Office upon request and payment of the necessary fee.

DETAILED DESCRIPTION OF THE INVENTION

Figure 1:
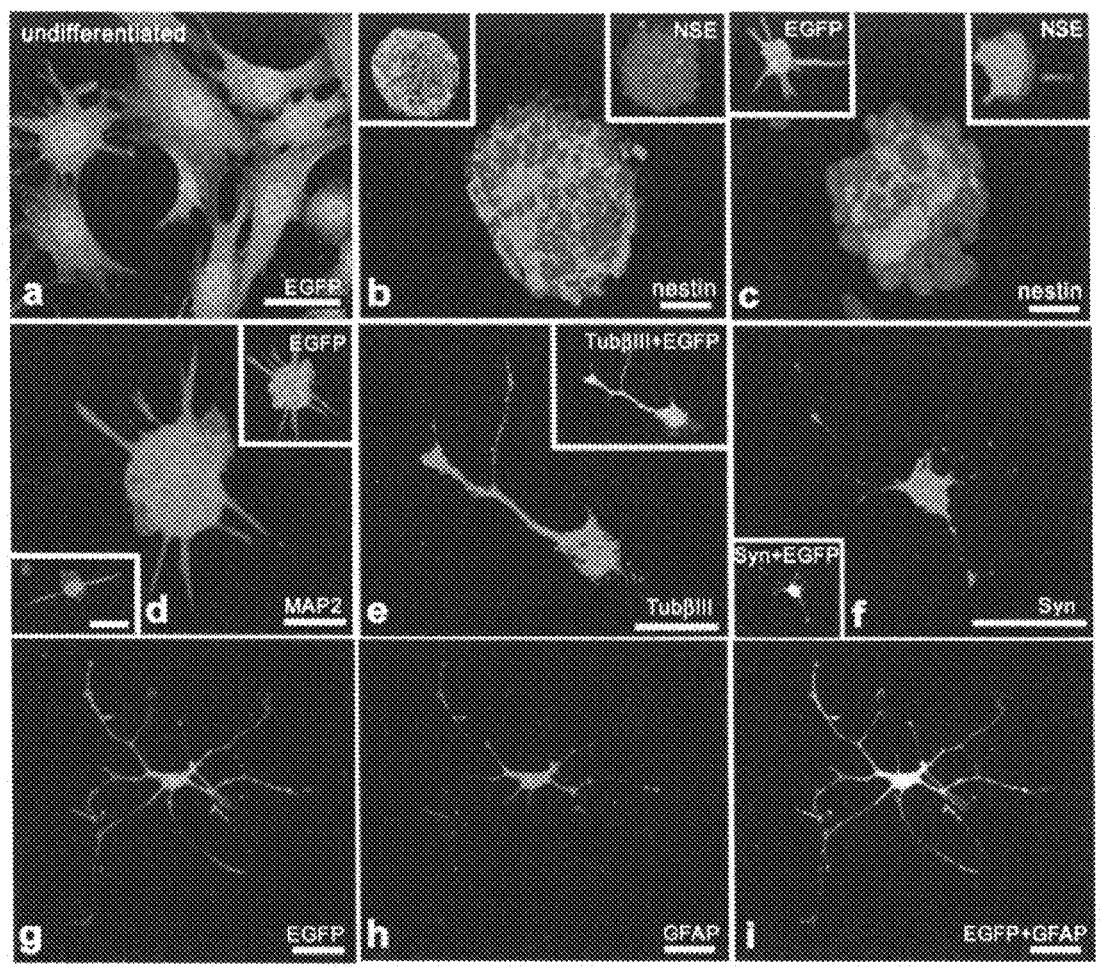
FIG. 1 is a photomicrograph showing immunocytochemical detection of neural proteins in MAPCs. Undifferentiated MAPCs derived from adult transgenic mice appear as large, flat fibroblast-like cells that express high levels of the green fluorescent protein reporter, EGFP (a, green). Four day expansion of MAPCs seeded at high density in the presence of retinoic acid (RA) and bFGF shows robust immunoreactivity of the progenitor cell marker, nestin (b, b left inset, red) but low levels of neuronal marker protein, NSE (b right inset, red) within cell spheres. Within 2 days following the withdrawal of mitogen factors, EGFP-positive MAPCs spheres (c left inset, red) differentiated in the presence of NGF and RA show reduced nestin immunoreactivity (c) and increased levels of the neuronal protein, NSE (c right inset, red). Following a six day differentiation, immunocytochemistry with antibodies to the late stage neuronal markers MAP2 (d, d left inset, red), tubulin βIII (e, e right inset, red) and synaptophysin (f, f left inset, red) showed intense labeling within EGFP-positive MAPC spheres (d right inset, green) and double-labeled MAPC monolayers with neuronal-like morphologies (e right inset, f left inset, yellow). Less than 1% of the differentiated EGFP-expressing MAPCs (g, green) were immunopositive with the glial marker, GFAP (h, red) when visualized by double label immunocytochemistry (i, yellow). Nuclei were stained by DAPI (blue) in all panels. Panels a-i, bar=50μ.

In general, the invention relates to marrow-derived adult progenitor cells (MAPCs) and their use in methods of treating various medical disorders, typically caused by or involving loss of cells or loss of cell function. These cells, when administered, e.g., intranasally, can cross the blood brain barrier and terminally differentiate into cholinergic neurons or otherwise localize and terminally differentiate.

Neural progenitor cells (NPCs) are stem cell populations found within the adult CNS (Gage, Science 287:1433-1438 (2000).), e.g., ependyma, subventricular zone, with the ability to develop neural lineage. Evidence suggests that NPCs also can be derived from a population of specialized mesenchymal cells in the adult bone marrow called, marrow-derived adult progenitor cells, (MAPCs) (Jiang et al., Nature 418:41-49 (2002), Verfaillie et al., Ann NY Acad Sci 996:231-234 (2003)). MAPCs with the ability to transdifferentiate into NPCs appear to be the most attractive for NPC isolation because MAPCs are more easily obtained than brain-derived NPCs, their use is not accompanied by the ethical setbacks encountered with ESCs, they can easily be obtained from adult donors and patients without tissue damage; and they have been used clinically for decades both safely and effectively. Additionally, recent studies have shown that pathologic conditions can promote the migration of MAPCs to an extent not previously appreciated in normal healthy brain tissue. MAPCs delivered by intravenous or intraperitoneal administration can rapidly cross the BBB and are capable of site-specific migration, differentiation, and integration within the CNS (Brazelton et al., (2000), Mezey et al., (2000)). When directly transplanted into brain, MAPCs differentiate into cells that express neuronal and glial-specific markers (Brazelton et al., (2000), Mezey et al., (2000)). Importantly, MAPCs have the added advantage of inherent host compatibility (Sanchez-Ramos, J. Neurosci. Res. 69:880-893 (2002)). In vitro, MAPCs can be expanded efficiently for greater that 100 doublings (Verfaillie et al., (2003)), proliferate without loss of differentiation potential, are not affected by senescence, and exhibit many traits of embryonic stem cells. The random differentiation of MAPCs can be spontaneously induced in the absence of the mitogen factors; however, neural differentiation can be promoted using retinoic acid (RA), nerve growth factor (NGF), brain derived neurotrophic factor (BDNF), neurotrophin-3 (NT3), glia derived neurotrophic factor (GDNF), ciliary neurotrophic factor (CNTF), basic-fibroblast growth factor (bFGF), FGF8, and/or sonic hedgehog (Shh) and yields neurons of primarily GABAergic and glutaminergic phenotypes (Jiang et al., (2002), Verfaillie et al., (2000). In vivo application of these cells has been reported previously (Brazelton et al., (2000), Mezey et al., (2000), Arai et al., Brain Res. 642:132-136 (1994)) and confirms their ability to express various neuronal marker proteins as well as their capability for migration and integration within the nervous system.

The use of MAPCs for neural lineage development and for cell-mediated trophic factor delivery represents a novel strategy toward reducing brain dysfunction and promoting neural regeneration and protection. Therapeutic approaches that attempt to promote the genesis of neural lineage cells and enhance neuroprotection by rescuing disease-specific neural cell dysfunction or death could treat cognitive aging and a host of neurological disorders in which there is a reduction in specific neuronal populations, glial cells or specific trophic factors critical for cellular homeostasis.

As MAPCs can differentiate into cells other than NPCs, administration of MPACs will be also useful in treating medical disorders involving non-neuronal cells, such as hepatocytes (Jiang et al., Zhonghua Yi Xue Za Zhi 87:414-418 (2007)), smooth muscle cells (Ross et al., J Clin Invest 116: 3139-3149 (2006)), and hematopoietic lineage cells (Serafini et al., J Exp Med 204(1):129-139 (2007)).

Diseases and Conditions

The MAPCs can be used to treat medical disorders, e.g., those caused by cell loss or loss of cell function. Exemplary medical disorders include developmental and degenerative diseases, such as a neurodevelopmental or neurodegenerative disorder, e.g., Alzheimer disease, Down's syndrome, Frontotemporal dementia, Niemann-Pick's disease, Parkinson's disease, a disorder selected from the group consisting of a polyglutamine expansion disorder (e.g., HD, dentatorubro-pallidoluysian atrophy, Kennedy's disease (also referred to as spinobulbar muscular atrophy), and spinocerebellar ataxia (e.g., type 1, type 2, type 3 (also referred to as Machado-Joseph disease), type 6, type 7, and type 17)), another trinucleotide repeat expansion disorder (e.g., fragile X syndrome, fragile XE mental retardation, Friedreich's ataxia, myotonic dystrophy, spinocerebellar ataxia type 8, and spinocerebellar ataxia type 12), Alexander disease, Alper's disease, amyotrophic lateral sclerosis, ataxia telangiectasia, Batten disease (also referred to as Spielmeyer-Vogt-Sjogren-Batten disease), Canavan disease, Cockayne syndrome, corticobasal degeneration, Creutzfeldt-Jakob disease, ischemia stroke, Krabbe disease, Lewy body dementia, multiple sclerosis, multiple system atrophy, Pelizaeus-Merzbacher disease, Pick's disease, primary lateral sclerosis, Refsum's disease, Sandhoff disease, Schilder's disease, spinal cord injury, spinal muscular atrophy, Steele-Richardson-Olszewski disease, and Tabes dorsalis.

MAPCs are also useful for the repair of neural or glial cell loss or loss of function that may be involved in the genesis of other brain disorders, including, for example, depression, bipolar disorders, schizophrenia, schizoaffective disorder, and anxiety disorders (e.g., panic disorder and post traumatic stress disorder). MAPCs exposed to growth factors may replace or restore functional deficits or cell loss in each of these conditions.

The remediation of disorders of the brain and nervous system in which there is an age-related, environmental or genetic reduction in neuronal or glia cells is provided by the invention. Each of these disorders is associated with cell loss which might be ameliorated by the neural transdifferentiation capabilities of MAPCs or their ability to function as vehicles of trophic factor delivery. For example, the severe neurodegeneration of cholinergic neurons in the basal forebrain is a pathologic hallmark of AD. Accompanying this targeted cell loss is a reduction in the levels of a potent growth factor, sAAPα, in the brains and CSF of AD patients, which seems to correlate with the cognitive deficits with the disease.

In addition to being useful to treat neurodegenerative disorders, MAPCs of this invention, when administered to a patient, are also sufficient to treat ischemia related disorders. Ischemia can occur in any tissue or organ including, for example, heart, brain, intestine, liver, kidney, muscle, and eye, and can be due to any number of causes including, for example, vascular occlusion (caused by, e.g., plaque formation or thrombosis) or other injury. Thus, specific examples of ischemia-related diseases or conditions include heart attack, myocardial ischemia, stroke, diabetic ischemia, critical limb ischemia, and intestinal ischemia.

MAPCs are also useful for treating a patient diagnosed with muscular dystrophy or skeletal muscle atrophy. Examples of muscular dystrophy are Duchenne muscular dystrophy, Becker muscular dystrophy, Emery-Dreifuss muscular dystrophy, limb girdle muscular dystrophy, myotonic dystrophy, oculopharyngeal muscular dystrophy, and distal muscular dystrophy.

MAPCS are also useful for treating a patient diagnosed with, or at risk of developing, diabetes or an autoimmune disease.

Administration

In addition to intraarterial or intravenous injection, several methods for administering cells to a patient are well established. Possible methods of administration for diseases include intracerebral, intrathecal, and intranasal administration. For muscular degeneration diseases, intramuscular injection can be used.

The cells of the invention are administered to a subject (e.g., a mammal, such as a human) in an effective amount, which is an amount that produces a desirable result in a treated subject (e.g., slowing or reversal of neurodegeneration, slowing or reversal of muscular degeneration, growth of tissue damaged by ischemia, or increase in reduced cell function, e.g., insulin secretion). Such therapeutically effective amounts can be determined empirically by those of skill in the art. Although the range can vary considerably, a therapeutically effective amount may be in the range of from 500 to $1\times10^6$ cells per kg body weight of the subject. The cells will be delivered in a pharmaceutically acceptable formulation, e.g., suspended in sterile saline.

Intranasal Administration

Traditionally, preparations of adult MAPCs are introduced to the brain by direct intracerebral, intracerebroventricular or intrastriatal microtransplantation or administered systemically by intraperitoneal, intraarterial, or intravenous delivery (Brazelton et al. (2000); Chen et al., Neuropharmacology 39:711-716 (2000); Hellmann et al., Neurosci Lett 395:124-128 (2006); Honma et al., Exp Neurol 199:56-66 (2006); Li et al., Neurosci Lett 316:67-70 (2001); Lu et al., J Neurotrauma 18:813-819 (2001); Willing et al., J Neurosci Res 73:296-307 (2003); Woodbury et al., J Neurosci Res 61:364-370 (2000)). MAPCs delivered to brain by each of these methods are capable of generating cells of neural lineage, but the number of cells and ultimately the robustness of the donor engraftment vary markedly with the route of administration. When given by the least invasive route, systemic administration, fewer than 1% of the total number of cells derived from bone marrow distribute to the brain (see Brazelton et al., 2001; Gage, Science (2000); Jiang et al., (2002); Lee et al., Mol Ther 3:857-866 (2001); Mezey et al., (2000); Poulsom et al., J Pathol 197:441-456 (2002); Verfaille et al., (2003); Woodbury et al., 2000 for review)).

The blood brain barrier (BBB) is composed of endothelial cells connected by tight junctional complexes that restrict the passage of most substances from blood to brain (reviewed in Ballabh et al., Neurobiol Dis 16:1-13 (2004). While the presence of an intact BBB is protective and impedes the entry of undesirable materials to brain, it also prevents the use of many therapeutic agents for the treatment of CNS disorders. Numerous studies have shown that the nasal mucosa provides a unique pathway for entry into the CNS that circumvents the BBB. It is evident from these studies that a host of substances (Graff and Pollack, J Pharmacol Sci 94:1187-1195 (2005); Illum, Eur J Pharm Sci 11:1-18 (2000); Liu et al., Neurosci Lett 308:91-94 (2001); Liu et al., J Neurol Sci 18:91-97 (2001); Mathison et al., J Drug Targ 5:415-441 (1998); Merkus et al., Neurology 60:1669-1671 (2003); Thorne et al., Clin Pharmacokinet 40:907-946 (2001); Turker et al., Pharm World Sci 26:137-142 (2004)) including not only small and large molecules but, also, viruses and bacteria can be delivered to the olfactory bulbs, and that, in some instances, these substances travel further into the brain, via nose-to-brain transport pathways (Graff and Pollack, 2005; Illum, 2000; Liu et al., 2001a and b; Mathison et al., 1998; Merkus et al., 2003; Thorne et al., 2001; Turker et al., 2004). Given the fate and therapeutic implications of bone marrow derived adult progenitor cells (MAPCs) following systemic, intravenous delivery (Brazelton et al., 2000; Honma et al., 2006; Mezey et al., 2000; Willing et al., 2003; Woodbury et al., 2000), we determined that MAPCs are able to enter the brain when administered by direct, non-invasive intranasal delivery.

Extending previous morphologic observations, we believe this is the first report showing that mammalian cells, specifically MAPCs, delivered by intranasal administration are capable of entering the olfactory bulb and brain.

Several transport pathways exist from the nasal epithelium to brain and include: 1) the olfactory nerve pathway; 2) the olfactory epithelial pathway; and 3) the systemic pathway (Mathison et al., 1998; Illum, 2000). The olfactory nerve pathway and the olfactory epithelial pathway provide direct passage to brain. The systemic pathway utilizes the systemic circulation, with substances or cells entering capillaries in either the respiratory or olfactory epithelium. Passage of materials through this route is generally slow due to limited movement through the BBB. Various studies have shown that most large molecular weight proteins are transported from the olfactory epithelium into the nasal cavity where they infiltrate the CSF, the olfactory bulb and deeper brain regions (reviewed in Graff and Pollack, 2005; Illum, 2000; Mathison et al., 1998; Merkus et al., 2003; Turker et al., 2004). The results of these studies suggest that these proteins enter the brain by extracellular routes because they enter these regions rapidly—within 8 to 10 mins.—compared to the transport of substances via the olfactory nerve, which has been shown to be slow—with substances reaching the brain within hours (reviewed in Graff and Pollack, 2005; Illum, 2000; Mathison et al., 1998; Merkus et al., 2003; Turker et al., 2004). Our findings indicate the rapid appearance of MAPCs within the olfactory bulb and the neocortex, which is consistent with the cells entering through the intercellular clefts in the olfactory epithelium, i.e. the glomerular cell layer, or extracellularly along the neurons to reach the CSF and the brain. This interpretation is also supported by the appearance of GFP-positive MAPCs in the order: nasal cavity→olfactory mucosa→olfactory bulb→CNS. More than likely, however, the passage of MAPCs into brain involves the use of more than one transport route. Although we have not directly compared the transport of MAPCs by different delivery routes in the same experiment, our studies of intravenous or intraventricular administration of stem cells in amounts ranging from 1 to $5 \times 10^5$ cells revealed fewer GFP-positive donor stem cells in brain at the same time points compared to the number detected following intranasal delivery.

Many factors are thought to play a role in MAPC migration into brain. One such factor is the chemokine, stromal cell-derived chemotactic factor-1 (SDF-1) which is released during inflammation or following cell injury (Hill et al., J Neuropathol Exp Neurol 63:84-96 (2004)) by microglial cells. SDF-1 is widely expressed in numerous tissues including brain where it is constitutively expressed in mature neurons and glia (Bajetto et al., J Neurochem 73:2348-2357 (1999); Bajetto et al., Front Neuroendocrinol 22:147-184 (2001); Ohtani et al., Neurosci Lett 249:163-166 (1998)). SDF-1 has been implicated in a host of physiological processes including glial proliferation, reactive gliosis, calcium mobilization, DNA synthesis, the stimulation of extracellular signal regulated kinases (ERK 1/2), and the homing of stem cells to regions of injury. Recent in vitro and in vivo studies have shown that mesenchymal stem cells exhibit SDF-1 dependent migration (Croitoru-Lamoury et al., J Interferon Cytokine Res 27:53-64 (2007); Gong et al., Cell Biol Int 30:466-471 (2006); Hill et al., 2004; Li et al., Biochem Biophys Res Commun 356:780-784 (2007); Menon et al., Stem Cells 25:520-528 (2007); Schmidt et al., Stem Cells 24: 1750-1758 (2006); Wynn et al., Blood 104:2643-2645 (2004)). The enhancement of MAPC entry and migration within lesioned animals could be due, at least in part, to SDF-1. Although a compelling argument can be made concerning the critical role of SDF-1 in regulating acute MAPC entry and site-specific migration, it is likely that SDF-1 acts synergistically with other growth factors to promote downstream effects that help to promote survival and subtype-specific neuronal differentiation.

The olfactory epithelium is unique in that it provides both intracellular and extracellular pathways into the CNS. Previous studies have described possible transport mechanisms of small and large substances administered by intranasal routes (see Graff and Pollack, 2005; Illum, 2000; Liu et al., 2001a and b; Mathison et al., 1998; Merkus et al., 2003; Thorne et al., 2001; Turker et al., 2004; for additional references). The anatomic details underlying these routes into the CNS following intranasal delivery are unclear. Although the routes of MAPC delivery to brain remain to be defined, the nasal delivery of MAPCs carrying growth factors or various neuropeptides may extend the limitations of the systemic administration of these substances in the treatment of brain disorders, particularly those whose pathology involves specific nerve or glial cell loss. Such disorders include stroke, brain injury, Alzheimer's disease, Parkinson's disease, Huntington's disease, schizophrenia and bipolar disorder, among others. Intranasal administration may prove to be a safer method for the therapeutic treatment of brain and spinal cord disorders than other delivery routes, such as intravenous administration or even less viable routes such as intracerebral, or intraventricular delivery which require surgery and the possible risk of infection. In addition, intranasal administration may be a more efficacious method of cell delivery which would rapidly enhance the biologic effects of these treatments, possibly lessening the amount of cells necessary to achieve therapeutic effects.

Progenitor Cells

Isolation of MAPCs is well known in the art (see for example: Gartner and Kaplan, Proc. Nat. Acad. Sci. USA 77:4756 (1980); Mauney et al., Tissue Engin. 10:81 (2004); Sutherland et al., PNAS 87:3584 (1990); Ramshaw et al., Exp Hematol. 29:981 (2001); Kassem, Ann NY Acad Sci., 1067: 436 (2006); Sotiropoulou et al., Stem Cells 24:1409 (2006); Romanov et al., Bull Exp Biol Med., 140:138 (2005); Alhadlaq and Mao, Stem Cell Dev. 13:436 (2004); Hung et al., Stem Cells, 20:249 (2002); Tondeau et al., Cytotherapy, 6:372 (2004); Smith et al., Stem Cells 22:823 (2004); Baxter et al., Stem Cells, 22:675 (2004)p; Jones et al., Arthritis Rheum., 46:3349 (2002); and Prockop et al., Cytotherapy, 3:393 (2001)).

In alternative embodiments and depending on the medical disorder, the cells administered can be selected from neural stem cells, muscle stem cells, satellite cells, liver stem cells, hematopoietic stem cells, bone marrow stromal cells, epidermal stem cells, embryonic stem cells, mesenchymal stem cells, umbilical cord stem cells, precursor cells, muscle precursor cells, myoblast, cardiomyoblast, neural precursor cells, glial precursor cells, neuronal precursor cells, hepatoblasts, neurons, oligodendrocytes, astrocytes, Schwann cells, skeletal muscle cells, cardiomyocytes, or hepatocytes. Such cells may be produced from in vitro differentiation of MAPCs, as is known in the art, or through isolation from an appropriate animal.

Trophic Factors

Trophic factors may be used in the methods of the invention in conjunction with MAPCs. For example, we have identified the use of MAPCs as vehicles of trophic factor delivery, e.g., for the autologous and non-invasive treatment of disease, and in particular, we have determined that MAPCs expressing recombinant human sAPPα protein can be used to treat neurodegenerative diseases.

MAPCs may be engineered to express trophic factors. These factors can promote the lineage specific differentiation of the recombinant cells as well as promote cell growth and survival of endogenous cells in the diseased tissue. In alternative embodiments, MAPCs may be contacted with trophic factors in vitro prior to administration, e.g., to promote differentiation, survival in vivo, or growth. Trophic factors may also be administered with the MAPCs, either in the same formulation or a different formulation. When different formulations are employed, administration of the trophic factor may or may not be concomitant with administration of the MAPCs. Expression of a trophic factor may also be induced in MAPCs from endogenous genes. Furthermore, trophic factors may be administered at intervals after administration of MAPCs in any of the methods of the invention.

Examples of trophic factors useful in the treatment of neurodegenerative diseases are set forth in Table 1. The expression of these factors promotes the development of MAPCs into neural progenitor cells (NPCs) followed by the terminal differentiation of these cells into neurological cells. In order to confirm the differentiation of MAPCs into desired cell types, the expression of specific markers can be measured. For example, increases in nestin indicate neural progenitor cells, increases in neuron specific nuclear protein (NeuN) or neuron specific enolase (NSE) indicate neuronal cells, and increases in glial fibrillary acidic protein (GFAP) or galactocerebroside (GALC) indicate glial cells (Jiang et al., (2000), Verfaillie et al., (2003), Woodbury et al., (2000)). Additionally, differentiation into NPCs is indicated by the increased expression of neuronal genes and transcription factors (e.g., sox-1, otx-1, otx-2, pax-2, pax-5, nestin, neuron specific enolase (NSE), nurr-1, glial fibrillary acidic protein (GFAP), myelin basic protein (MBP) (Jiang et al., (2002), Verfaillie et al., (2003), Woodbury et al., (2000)).

TABLE 1

Genes for Transfection of Progenitor Cells

| Name | Description | Exemplary Genebank Acc. Nos. |
|---|---|---|
| Receptors | | |
| TrkA | Primary receptor for Nerve Growth Factor | Y09028 |
| EGFR | Epidermal Growth Factor Receptor | NM_005228 |
| IGFR | Insulin-like Growth Factor Receptor | M69229 |
| TrkB | Receptor for Nerve Growth Factor | AF410902 |
| Notch 1-4 see Cell Fate, notch family | cell-cell communication (developmental) | NM_01761, NM_024408, NM_000435, NM_004557 |
| Enzymes | | |
| sAPPa | alpha secretase of APP | |
| BCHE | butyrylcholinesterase | M16541 |
| ChAT | Choline Acetyl-transferase | AF305907 |
| Acetyl CoA | Coenzyme A | NM_001607 |
| GSKb | Wnt Signalling Enzyme | BC012760 |
| Cell Proliferation | | |
| CHRM Family | Cholinergic Receptor (Muscarinic) 1 | Y00508, U29589, M16405 |
| EGF | Epidermal Growth Factor | X04571 |
| FGF Family | Fibroblast Growth Factor | X59065, J04513, M17446, M23534, X63454, NM_002009, D38752, D14838, NM_004465, U66197, BC034340, AB009391, AB009249, AB007422, AB018122, AB030648, AB021975, AF263537, |
| IL3 | Interleukin-3 | M14743 |
| VEGF | Vascular Endothelial Growth Factor | AAA35789 |
| CDK1 | Cyclin Dependent kinase | |
| CDK5RAP Family | regulatory subunit associated protein | AF152097, BK005504, AF110322 |
| FGF5 | Fibroblast Growth Factor | M23534 |
| MYT2 | myelin transcription factor | AF006822 |
| S100 Family | | BC014392, BC002829, BC012893, BC016300, Z18954, BC001431, BC034687, AY189118, NM_002963, BC005928, BC047681, BC015973, D38583, AC004668, BC070294, AK097132, AY007220, BC010541, M59488 |
| Cell Migration/Motility | | |
| NTF Family | Neurotrophin | BC068030, M73238, 1889806, 1496419, M86529, S41540, S41541, |
| Cell Fate | | |
| NOTCH Family | notch homolog | AF308602, AF315356, NM_203458, U97669, |
| SHH | Sonic Hedgehog | NM_000193 |

TABLE 1-continued

Genes for Transfection of Progenitor Cells

| Name | Description | Exemplary Genebank Acc. Nos. |
|---|---|---|
| NEUROD Family | Neurogenic bHLH | U50823, U58681, AF203901, NM_022728 |
| NEUROG Family | Neurogenin | U63842, AF303002, AJ133776 |
| NHLH Family | nescient helix loop helix | BC013789, NM_005599 |
| NRG1 | neuregulin | L12261 |
| Growth Factors | | |
| BDNF | brain-derived neurotrophic factor | NM_170735 |
| FGF Family | Fibroblast growth Factor | See above |
| GDF11 | Growth differentiation factor | AF100907 |
| GDNF | glial cell derived neurotrophic factor | NM_199234, NM_199231, NM_000514 |
| GPI | glucose phosphate isomerase | M61214 |
| NRTN | neurturin | U78110 |
| PDGF Family | Platelet-Derived Growth Factor | XM_930866, NM_033016, AF091434 |
| Other Genes | | |
| GFAP | glial fibrillary acidic protein | S40719 |
| GSS | glutathione synthetase | NM_000178 |
| SOD1 | Superoxide dismutase | NM_000454 |

The α-Secretase Cleavage Product of APP, sAPPα

The amyloid precursor protein (APP) is a transmembrane protein that is highly expressed during development and in the adult nervous system (Arai et al., Brain Res. 642:132-136 (1994)). The amyloidogenic processing of APP occurs through the action of β and γ secretases and generates the Aβ peptide (Sinha and Lieberburg, Proc. Natl. Acad. Sci. USA 96:11049-11053 (1999)). The β-secretase cleavage of APP produces a soluble secreted fragment called sAPPβ. By contrast, the non-amyloidogenic processing of APP by α-secretase cleaves within the Aβ domain precluding Aβ peptide formation (Esch et al., Science 248:1122-1124 (1990)) and releasing soluble sAPPα.

A reported characteristic of sAPPα is its potent neurotrophic activity and its ability to synergistically enhance the neuritogenic and neuroprotective activities of NGF in certain neuron types (Mattson, J. Neurobiol. 25:439-450 (1994), Araki et al., Biochem. Biophy. Res. Commun. 181:265-271 (1991)). The trophic effects of sAPPα have been reported to be approximately 100-fold more potent than sAPPβ (Furukawa et al., J. Neurochem. 67:1882-1896 (1996)) suggesting that the amyloidogenic processing of APP may promote neurodegeneration by increasing Aβ and reducing sAPPα simultaneously. sAPPα may also support neurogenesis and synaptic plasticity in vivo (Mucke et al., Brain Res. 666:151-167 (1994)). Transgenic, plaque-forming mice that overexpress the α-secretase, ADAM 10, exhibit significant increases in sAPPα in the CNS (Postina et al., J. Clin. Invest. 113:1456-1464 (2004)); this increase is accompanied by reduced Aβ peptide burden and alleviation of LTP and cognitive abnormalities (Postina et al., J. Clin. Invest. 113:1456-1464 (2004)). Recently, it was shown that plaque-forming mice on chronic dietary restriction have a reduced amyloid burden accompanied by a significant elevation of sAPPα (Wang et al., FASEB J. 19:659-661 (2005)). Direct infusion of sAPPα into rodent brain increases synaptic density and maybe involved in processes involved in early memory formation (Roch et al., Proc. Natl. Acad. Sci. USA 91:7450-7454 (1994)). In AD brains and CSF, the levels of sAPPα are significantly reduced (Van Nostrand et al., Proc. Natl. Acad. Sci. USA 89:2551-2555 (1992), Lannfelt et al., Nat. Med. 1:829-832 (1995)).

Nerve Growth Factor

The neurotrophin, nerve growth factor (NGF), acts on cholinergic neurons (Hefti, J. Neurosci 6:2155-2162 (1986), Barde, Prog. Clin. Biol. Res. 390:45-56 (1994)), particularly those in basal forebrain areas that release the majority of acetylcholine to the cerebral cortex and hippocampus, and promotes their functional and survival abilities. sAPPα is required for the activation of the p75NGFR signaling by NGF in these cell populations. The synergistic effect of sAPPα on the neurotrophic and protective activities of NGF (Hefti, J. Neurosci. 6:2155-2162 (1986), Luo et al., J. Neurosci. Res. 63:410-420 (2001)) is thought to occur by the ability of sAPPα to facilitate the binding of NGF to its receptors thereby elevating its capacity to maintain a neuronal phenotype. The severe neurodegeneration of cholinergic neurons in the basal forebrain is a pathologic hallmark of AD (Whitehouse et al., Psychopharmacol. Bull. 19:437-440 (1983)). Accompanying this targeted cell loss is a reduction in the levels of sAPPα in the brains and CSF of AD patients, which seems to correlate with the cognitive deficits with the disease (Van Nostrand et al., Proc. Natl. Acad. Sci. USA 89:2551-2555 (1992), Lannfelt et al., Nat. Med. 1:829-832 (1995)).

We examined the ability of sAPPα to enhance the NGF/RA-induced transdifferentiation of MAPCs into neural cells and cholinergic neuronal phenotypes. Our data demonstrate that sAPPα potentiates the neurotrophic effects of NGF and RA on MAPC neuronal development by increasing the expression of early and late stage neuronal marker proteins and the appearance of cell-to-cell synaptic-like contacts and by promoting the terminal maturation of MAPCs to neurons exhibiting a cholinergic phenotype. Further, we find that in vivo intravenous delivery of sAAPα by MAPCs reduced the loss of brain regions rich in cholinergic neurons detected by MRI in an animal model with AD-relevant age-related neurodegeneration.

Because the levels of sAPPα are decreased in AD (Van Nostrand et al., (1992), Lannfelt et al., (1995)) and cholinergic neurons are severely vulnerable to degeneration in AD (Whitehouse et al., (1983)), the present work suggests that the combined use of sAPPα and MAPCs offers a new and powerful therapeutic strategy that would prevent cell loss and restore function in AD.

The value of NGF in reducing cholinergic cell death in AD has long been suggested and several very recent phase 1 clinical studies now support the use of NGF as a possible long-term therapeutic agent with the capability of modifying neurodegeneration and subsequently improving cognitive decline (Longo and Massa, J. Alzheimers Dis 6:S13-17 (2004), Tuszynski et al., Nat Med 11:551-555 (2005)). In combination with these previous studies, the present work provides an important step in optimizing AD therapy by identifying sAPPα as a factor that enhances the differentiation of adult bone marrow progenitor cells into the same distinct neuronal subtypes lost as a function of AD neurodegeneration and possibly providing an unlimited source of neurons for AD treatment.

For medical conditions, e.g., caused by cell loss or loss of cell function, other than neurodegenerative diseases, MAPCs may be engineered to express trophic factors that encourage differentiation into the lost or nonfunctional cells. Alternatively, cells may be contacted with such trophic factors in vitro prior to administration.

Methods of Recombinant Expression

The invention features the method of ex vivo gene therapy to express a growth factor (e.g., sAPPα) in a patient. In ex vivo gene therapy, cells (e.g., MAPCs) are removed from the patient and treated with a vector to express the gene of interest. In this method of gene therapy, the treated cells are then re-administered to the patient.

Numerous different methods for recombinant expression are well known in the art. These methods include, but are not limited to, the use of DNA plasmid vectors as well as DNA and RNA viral vectors. In the present invention, these vectors are engineered to express a growth factor (e.g., sAPPα) when integrated into patient cells.

Adenoviruses are able to transfect a wide variety of cell types, including non-dividing cells. The invention includes the use of any one of more than 50 serotypes of adenoviruses that are known in the art, including the most commonly used serotypes for gene therapy: type 2 and type 5. In order to increase the efficacy of gene expression, and prevent the unintended spread of the virus, genetic modifications of adenoviruses have included the deletion of the E1 region, deletion of the E1 region along with deletion of either the E2 or E4 region, or deletion of the entire adenovirus genome except the cis-acting inverted terminal repeats and a packaging signal (Gardlik et al., Med Sci Monit. 11:RA110-121, (2005).

Retroviruses were among the first constructed human gene therapy vectors and, in general, are not able to transfect non-dividing cells. The invention includes use of any appropriate type of retrovirus that is known in the art, including, but not limited to, Moloney Murine Leukaemia Virus (MoMLV). The invention further embodies genetic modification of retroviruses including deletions of the gag, pol, or env genes.

In another aspect, the invention features the methods of gene therapy that utilize a lentivirus vectors to express a growth factor (e.g., sAPPα) in a patient. Lentiviruses are a special group of retroviruses with the ability to infect both proliferating and quiescent cells. An exemplary lentivirus vector for use in gene therapy is the HIV-1 lentivirus. Previously constructed genetic modifications of lentiviruses include the deletion of all protein encoding genes except those of the gag, pol, and rev genes (Moreau-Gaudry et al., Blood. 98:2664-2672, (2001)).

Adeno-associated virus (AAV) vectors can achieve latent infection of a broad range of cell types (e.g., MAPCs and NPCs), exhibiting the desired characteristic of persistent expression of a therapeutic gene in a patient. The invention includes the use of any appropriate type of adeno-associated virus known in the art including, but not limited to AAV1, AAV2, AAV3, AAV4, AAV5, and AAV6 (Lee et al., Biochem J. 387:1-15, (2005)).

Methods of ex vivo gene therapy using cationic liposomes are also well known in the art. Exemplary cationic liposomes for use in this invention are DOTMA, DOPE, DOSPA, DOTAP, DC-Chol, Lipid GL-67™, and EDMPC. These chemicals can be used individually, or in combination, to transfect human cells with a plasmid constructed to express a trophic factor (e.g., sAPPα).

Another aspect of this invention is the methods of gene therapy that utilize DNA-polymer conjugates for the expression of a growth factor in a patient. In this aspect of the invention, a vector constructed to express a trophic factor in a patient is combined with a polymer to achieve expression of a trophic factor without using a viral vector. Exemplary compounds for use in this embodiment of the invention are polyethyleneimine (PEI), polylysine, polylysine linked to nuclear localization signals, polyamidoamine, or polyarginine ($Arg_{16}$).

Another method of gene therapy uses a substantially purified DNA vector (naked DNA) for the expression of a protein of interest in a patient. This aspect of the invention features a treatment where the naked DNA is administered using, for example, electroporation.

The above vectors can be constructed to constitutively express a trophic factor protein (e.g., sAPPα). Numerous constitutive regulator elements are well known in the art. Often, elements present in the native viruses described above are used to constitutively express a gene of interest. Other examples of constitutive regulatory elements are the chicken β-actin, EF1, EGR1, eIF4A1, FerH, FerL, GAPDH, GRP78, GRP94, HSP70, beta-Kin, ROSA, and ubiquitin B promoters.

Combination Therapy

The administration of MAPCs can also be done in combination with any of the compounds listed in Tables 2 or 3. These compounds can be directly administered to the patient (e.g., through intravenous injection) or, in certain instances, be recombinantly expressed in MAPCs in combination with one of the above listed trophic factors.

TABLE 2

Growth/Transcription Factors and Signaling Molecules

| Name | Description |
| --- | --- |
| NGF | Nerve Growth Factor |
| proNGF | Nerve Growth Factor Precursor |
| FGF | Fibroblast Growth Factor |
| IGF | Insulin-like Growth Factor |
| LIF | Leukemia Inhibitory Growth Factor |
| BDNF | Brain-Derived Neurotrophic Factor |
| CNTF | Ciliary Neurotrophic Factor |
| SHH | Sonic Hedgehog (developmental) |
| Sortilin | Binds to proNGF and p75, proapoptotic |
| Int-2 | Epithelial Growth Factor |
| Wnt | Wnt Signalling Pathway (developmental) |
| b-catenin | Signal Transduction |
| GDNF | Glial Derived Neurotropic Growth Factor |
| p75 | Low Affinity Neurotrophin Receptor |
| NT-3 | Neurotrophin-3 |
| NT-4 | Neurotrophin-4 |

TABLE 2-continued

Growth/Transcription Factors and Signaling Molecules

| Name | Description |
| --- | --- |
| FGF-1 or aFGF | Acidic Fibroblast Growth Factor |
| PDGF | Platelet Derived Growth Factor |
| TGF | Transforming Growth Factor |
| TNF | Tumor Necrosis Factor |
| Delta | cell-cell communication (developmental) |
| Chemokines | Induce chemotaxis, pro-inflammatory |
| RA | Retinoic acid |

Examples of pharmaceutical compounds which are useful in combination with the cells of the invention are listed in Table 3.

TABLE 3

Pharmaceutical Compounds

| Name | Description |
| --- | --- |
| Antidepressants | Affect acetylcholinesterase |
| Galantamine (Reminyl) | Regulates cholinergic system, acts on nicotinic receptors |
| Tacrine (Cognex) | cholinergic regulator |
| NSAIDS | Non Steroidal Anti-Inflammatory Drugs |
| SSRI's (Fluoxetine HCl, etc.) | Selective Serotonin Reuptake inhibitors |
| Rolipam | cAMP Phosphodiesterase Inhibitor |
| Cerebrolysin | Mimics NGF activity |
| Leteprinim Potassium | Increases NGF production |
| Neuroleptics (phenothiazines) | Block dopamine, acetylcholine, serotonin, histamine, and NE |
| beta and gamma secretase inhibitors | Block APP cleavage |
| Lithium | Mood Stabilizer |
| Valproate | Mood Stabilizer, anticonvulsant |
| statins | Cholesterol Lowering |
| Atypical Neuroleptics | Risperidone, Halperidol, Olanzapine, etc. |
| Neurotransmitter mimetics | carbachol (mimics acetylcholene) |

EXAMPLES

Methods

Marrow-derived Adult Progenitor Cells (MAPC) Cultures

Bone marrow was harvested from the femurs of six 7-week-old male transgenic mice expressing enhanced green fluorescent protein (EGFP; Jackson Laboratories, Bar Harbor, Me.). The hematopoietic portion of the bone marrow was depleted as described previously (Jiang et al., (2002)). Marrow-derived adult progenitor cells (MAPCs) were maintained undifferentiated by mEGF/bFGF/mLIF (Chemicon). Prior to differentiation, the identity of MAPCs was confirmed by negative staining with the hematopoietic marker, CD45. The presence of the GFP tag could be confirmed by fluorescence.

Differentiation of MAPCs

MAPCs were seeded on coverslips coated with poly-D-lysine (Sigma, 20 µg/ml) and laminin (Becton Dickinson, 1 µg/ml). Neural differentiation was induced by DMEM/F12 supplied with B27 (Gibco), dexamethasone (Sigma, 1 nM), ascorbic acid 2-phosphate (Sigma, 0.1 mM), all-trans retinoic acid (Sigma, 2 µM), nerve growth factor (Chemicon, 20 ng/ml), and antibiotics. The bacterially (10 nM) or eukaryotically (3 nM) expressed form of the soluble α-secretase cleaved amyloid precursor protein, rh-sAPPα (S. Barger), was used to evaluate the effects of sAPPα on MAPC neural differentiation. The cells were treated for 2 to 6 days, and the medium were changed every 2 days.

Transgenic Mice and Injections

Both sexes were used in this study. Transgenic mice expressing both a chimeric amyloid precursor protein ($APP_{Swe}$) and human presenilin 1 (A246E variant) (PS/APP; n=6, 6 to 8 months of age) were obtained from the Jackson Laboratory, Bar Harbor, Me. An equal number of non-transgenic mice (B6C3F1/J) were used as controls (nonTg; n=6; 6 to 8 months of age). Each mouse received one injection containing $1 \times 10^6/50$ µl of either untransfected MAPCs (n=3) or MAPCs transfected with rh-sAPPα (n=3) through the tail vein using a 25 gauge needle.

For the intranasal administration studies, C57B16/J mice (n=27; Jackson Laboratories) of both sexes, aged 8 weeks, were divided into two groups. The first group consisted of 18 mice that were stab lesioned in the neocortex (AP: 0.7, ML: 1.5, DV: 1.2) or the caudate putamen (AP: 1.0, ML: 1.6, DV: 3.3). A second group consisted of seven age-matched mice that were lesioned in a similar fashion and served as controls. An additional nine mice did not receive lesions.

Immunocytochemical Studies

Immunocytochemical studies were performed as previously described (Cataldo et al., J. Neurosci 17:6788-6792 (2003)) on 40 µm vibratome coronal sections of aldehydes-fixed tissue of transgenic and nontransgenic mouse brains.

Primary antibodies directed against neuron-specific nuclear protein (NeuN; Chemicon, 1:250), glial fibrillary acidic protein (GFAP; Dako, 1:500), nestin (Santa Cruz, 1:500), tubulin βIII (Chemicon, 1:250), microtubule associated protein-2 (MAP2; Sigma, 1:250), neuron specific enolase (NSE; Chemicon, 1:500), and synaptophysin (Syn; Santa Cruz, 1:500) were used for immunocytochemistry. Alexa Fluor 568 conjugated secondary antibodies (Molecular Probes, 1:1000) were applied for immunofluorescence and confocal microscopy. DAPI staining was used in all cytochemical studies to identify cell nuclei. NuPAGE electrophoresis system (Invitrogen) was used for Western-blot assay and proteins were probed by antibodies (1:1000) directed against NSE, NeuN, 160 kD neurofilament (NFM; Zymed), synaptophysin, a synthetic peptide generated to the carboxy-terminal 22 amino acids of the amyloid precursor protein (CT695; Zymed), choline acetyltransferase (ChAT; Chemicon), and glutamate decarboxylase (GAD; Santa Cruz) and followed by alkaline phosphatase-conjugated secondary antibodies (Promega, 1:12,000) and Chemiluminescent detection (Applied Biosystems).

Quantification

For quantification analyses of NeuN-positive MAPCs differentiated with NGF and RA in the presence or absence of sAPPα, ten fields (greater than 200 cells) were selected at random from cellular monolayers plated at equal density for each sample. The percentage of NeuN-positive within individual cell samples was obtained by averaging the number of NeuN-positive cells per total number of cells identified by DAPI fluorescence in each of ten fields. At least three samples were counted for each of the two groups. Statistical computations were performed using a student's t-test. Differences in the levels of immunoreactive NSE, NeuN, synaptophysin, and NFM, APP695, CHAT, and GAD were quantified by scan analysis using NIH ImageJ 1.29 and statistical analysis were performed using the student's t-test.

Example 1

MAPCs obtained from the femurs of transgenic mice expressing enhanced green fluorescent protein (EGFP) and grown in the presence of the mitogen factors (bFGF, epidermal growth factor-EGF) and leukemia inhibitory factor (LIF) for over 120 doublings were negative for markers of hematopoietic precursor cells, i.e. CD45—a finding consistent with several previous studies (Jiang et al., (2002), Verfaillie et al., (2003)) and appeared as large fibroblast-like cells (FIG. 1).

The neural development of MAPCs was examined by withdrawing mitogen factors/LIF and maintaining cells in serum free medium containing 2 μm retinoic acid (RA) plus 20 ng/ml NGF. High density seeding, i.e. $1 \times 10^5$, of isolated MAPCs in the differentiation media resulted in the appearance of various size cellular aggregates, similar to neurospheres developed from brain derived NPCs, which were not adherent to the culture plates (FIG. 1). After 2 days, immunocytochemical analysis using an antibody to nestin, an intermediate filament protein found in neural progenitor cells (Lendahl et al., Cell 60:585-595 (1990)), showed moderate levels of nestin immunoreactivity and very low but detectable levels of the neuronal marker, neuron specific enolase (NSE; FIG. 1). The progressive transformation to neural lineage cells coincided with the loss of the flat, fibroblastic cell morphology, characteristic of the undifferentiated MAPCs, and the appearance of neuronal-like morphologies i.e. small round soma and simple branched processes, in differentiating MAPCs. After six days differentiation, the transition of MAPC derived NPC to neuronal-like cells was supported by the immunocytochemical expression of additional neuronal or glial marker proteins such as NSE, MAP2, β-tubulin III, synaptophysin (FIG. 1). The transdifferentiation of MAPCs to neurons was associated with the increased expression of the neuronal marker, NSE, and a decrease in nestin immunoreactivity. We found that that the majority of differentiated MAPCs exhibited morphologies consistent with neurons, whereas less than 1% of the differentiated MAPCs displayed phenotypes consistent with glia (GFAP-immunoreactive).

Figure 2:
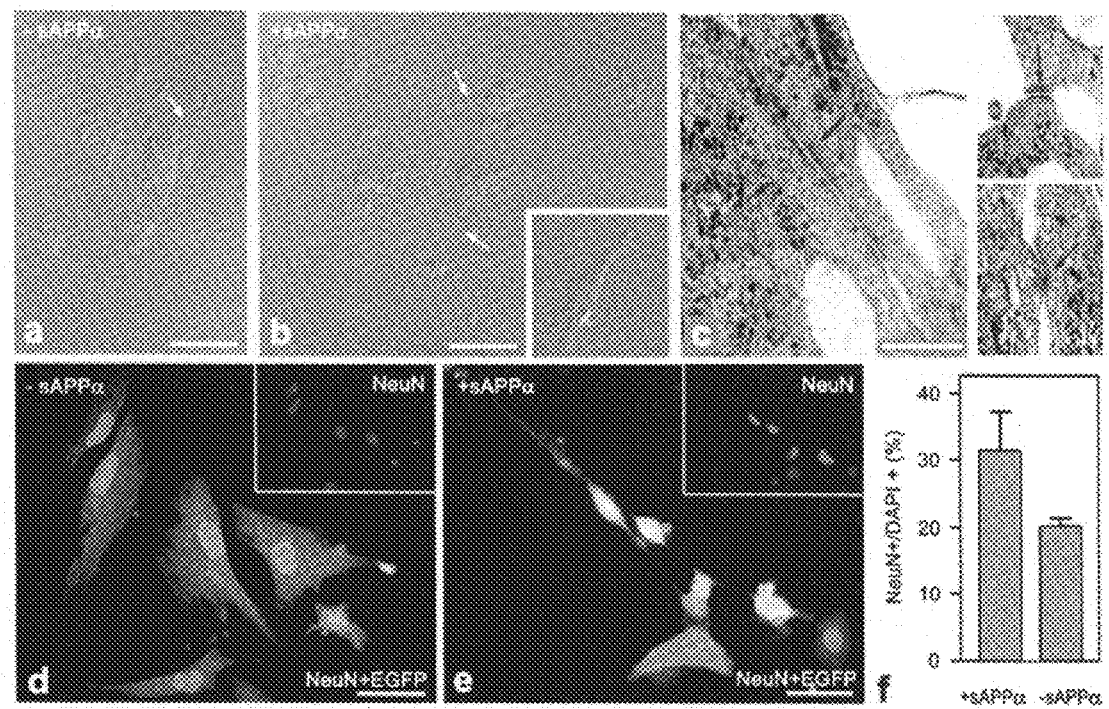
FIG. 2 is a photomicrograph and graph showing sAPPα enhances the neuronal development of MAPCs. Differential interference contrast photomicrographs of NPCs derived from MAPC spheres and differentiated for four days in the presence of sAPPα, NGF, and RA (b, b inset) showed higher numbers of spindle-shaped cells with prominent neurites (arrows) compared to cultures grown in NFG/RA without sAPPα (a). Some of sAPPα treated MAPCs showed pyramidal neuronal-like morphologies (b inset). Ultrastructural inspection of the sAPPα-treated MAPCs revealed the presence of two types of closely apposed neuronal junctional specializations—asymmetrical complexes, typical of synaptic complexes (c top inset, arrow) and symmetrical complexes with characteristics of puncta adhaerentia (c and c lower inset, arrows). Because the synapse in c is probably immature, it does not contain numerous synaptic vesicles. After four days differentiation, immunocytochemical analysis of sAPPα-treated MAPCs with the neuronal marker, NeuN, identified many small NeuN-positive cells (e and e inset). These same immunoreactive cells also displayed characteristic neuronal morphologies unlike the majority of MAPCs differentiated without sAPPα, which appeared as large NeuN-negative flattened cells (d and d inset). Cell nuclei shown by blue DAPI staining (d, e). Green fluorescence identifies the presence of the EGFP reporter (d, e). Panel f shows quantitative analysis of the number of immunoreactive cells from MAPC cultures differentiated in the presence or absence of sAPPα and immunostained with an antibody to NeuN. The y-axis represents the percentage of NeuN-positive cells over the total number of DAPI-positive cells. The values represent the means obtained from three separate experiments. Panels a, b, bar=30 µm; panel c, bar=5 µm; panels d, e, bar=50 µm.
Figure 3:
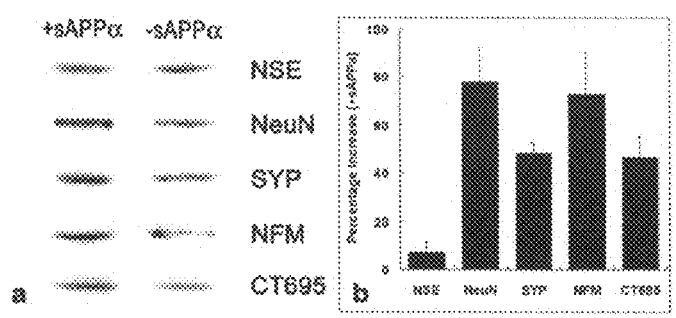
FIG. 3 is a western blot and graph showing sAPPα increases the levels of neuronal proteins in MAPCs. (a). Western blot analyses showing the levels of various neuronal proteins in lysates obtained from MAPCs differentiated with NGF/RA in the presence or absence of sAPPα. (b) Quantification of immunoreactive proteins measured in (a) shows the relative increase in immunoreactive protein levels in MAPC lysates with the addition of sAPPα. These results confirmed the immunocytochemical findings using antibodies to the same markers. The values represent the means of three independent experiments.

Next, we examined the influence of sAPPα on enhancing the NGF/RA-induced neuronal development of MAPCs. Cultures of MAPCs were differentiated for six days in serum-free media with NGF and RA in the presence or absence of sAPPα. The addition of sAPPα increased the numbers of MAPC-derived cells/field bearing neurites compared to cells differentiated with NGF/RA alone (FIG. 2). Ultrastructural examination showed that sAPPα promoted the appearance of other structural characteristics consistent with neurons including immature junctional specializations, i.e. puncta adhaerens, and synaptic complexes in which there is close apposition between the pre- and post synaptic membranes and asymmetrically disposed dense material (FIG. 2). In the later, the absence of synaptic vesicles, which are typical of mature synapses, suggests these complexes were crude and in the earliest stages of development. NGF/RA-induced MAPCs treated with sAPPα showed higher numbers of neuronal-like cells, i.e. round/ovoid cell bodies with processes, that were immunoreactive with the neuronal proteins, NeuN (FIG. 2) and β-tubulin III (not shown) compared to MAPCs differentiated with NGF/RA alone. Quantitative analysis to confirm the sAPPα effect on NGF/RA-induced MAPCs was performed by counting 10 to 12 fields of MAPCs (approximately 400 to 600 cells) in each of three culture dishes and determining the number of NeuN-immunoreactive (FIG. 2) or β-tubulin III-immunoreactive cells per total cells counted by DAPI nuclei stain. The percentage of NeuN-positive cells was nearly 2-fold higher and β-tubulin III-positive cells nearly 4-fold higher than MAPCs differentiated with NGF/RA alone (FIG. 2). We further validated both the immunocytochemical and morphometric findings by Western blot analysis and showed that the levels of immunoreactive neuronal proteins, including MAP2, synaptophysin, the 150 kDA molecular weight neurofilament protein, NFM and endogenous APP detected in the MAPCs differentiated with sAPPα for 6 days were 30% to 70% higher greater than the levels measured in MAPCs without sAPPα (FIG. 3).

Figure 4:
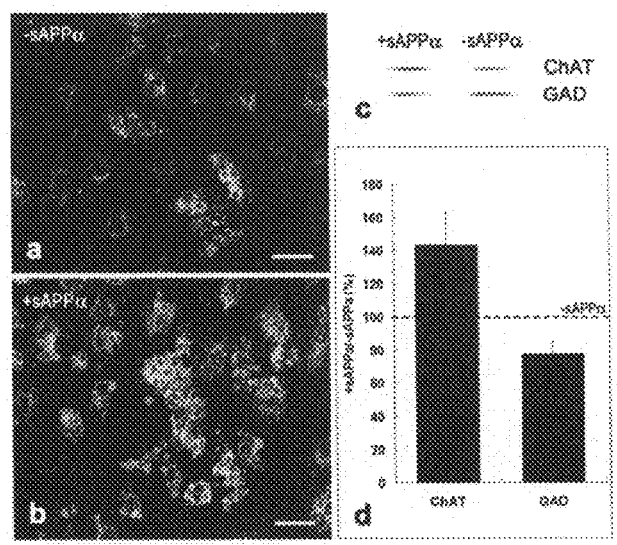
FIG. 4 is a photomicrograph, western blot, and graph showing sAPPα promotes the development of cholinergic neuron phenotypes from MAPCs. MAPCs differentiated in the presence of NGF/RA/sAPPα for six days displayed higher levels of immunoreactivity for the cholinergic marker, choline acetyltransferase (ChAT) (b) compared to MAPCs differentiated with NGF/RA in the absence of sAPPα (a). The immunocytochemical findings were confirmed by Western blot analysis (c) and quantitative densitometry and showed that in lysates prepared from equal numbers of MAPCs, immunoreactive ChAT levels were 43±20.3% higher in sAPPα-treated MAPCs compared to MAPCs differentiated without the addition of sAPPα. (d) In the same lysates, higher ChAT levels in sAPPα-treated MAPCs were accompanied by a 23%±7.6% reduction in the level of the GABAergic marker protein, GAD, vs MAPCs differentiated with NGF/RA only.

It is well established that neurotrophins, such as NGF/BDNF/NT3, enhance neurogenesis and prevent cell death (Lendahl et al., (1990)). NGF targets cholinergic cell populations particularly basal forebrain neurons that release the majority of acetylcholine in the cerebral cortex and hippocampus, and promotes their functional and survival abilities (Hefti, (1986), Barde, Prog. Clin. Biol. Res. 390:45-56 (1994)). sAPPα is required for NGF activity and in certain neuronal types, several studies have reported a synergistic effect of sAPPα on the neurotrophic and protective activities of NGF (Wallace et al., Brain Res. Mol. Brain Res. 52:201-212 (1997), Luo et al., (2001)). Based on this knowledge, we examined the possibility that sAPPα may enhance the neural development of MAPCs to cholinergic phenotypes. Immunocytochemistry of MAPCs differentiated in the presence of sAPPα using choline acetyltransferase (ChAT), a marker of cholinergic neurons, showed an increase in the number of ChAT-positive cells per field compared to MAPCs differentiated with NGF and RA only (FIG. 4). Western blots of cell lysates prepared from equal numbers of MAPCs and probed with ChAT, confirmed the immunocytochemical findings and showed a 43±20.3% increase in ChAT immunoreactive protein in sAPPα treated NGF/RA-induced MAPCs compared to MAPCs differentiated with NGF/RA demonstrating that sAPPα potentiates the NGF effects of differentiating MAPCs to induce a cholinergic neuronal phenotype (FIG. 4). Interestingly, the levels of the GABAergic marker, glutamate decarboxylase (GAD65/67), were 23±7.6% lower in sAPPα treated MAPCs compared with MAPCs differentiated with NGF/RA alone.

Figure 5:
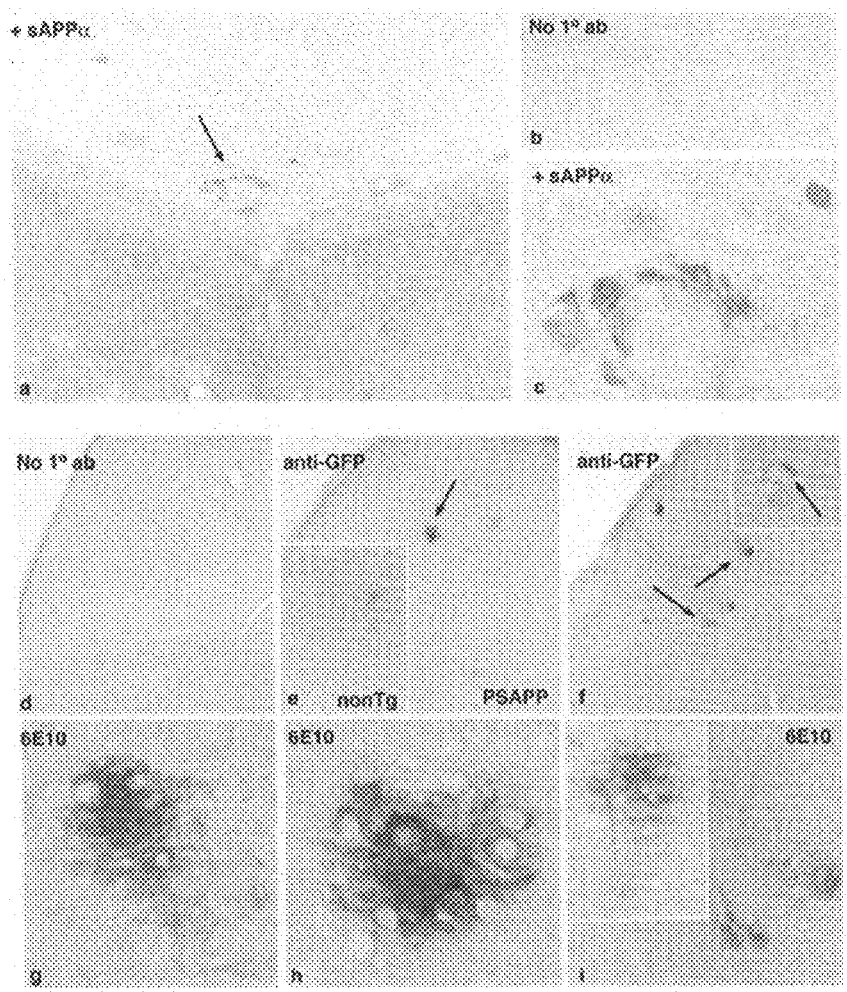
FIG. 5 is a photomicrograph showing distribution of MAPCs in mouse brain after i.v. injection. At 6 weeks post injection, MAPCs transfected with human sAPPα were detected in tissue sections from the brains of PS/APP and nonTg control (not shown) recipient mice using an antibody to human sAPPα, 6E10. Immunopositive cells were most frequently seen in close proximity to cerebral vasculature (a, arrow and c). The presence of MAPCs from GFP-expressing donor mice and transfected with sAPPα was detected 8 weeks postinjection in the brains of both non-transgenic (nonTg; e, inset) and the PS/APP mouse model of AD (f) by immunolabeling using an antibody to GFP. Immunoreaction product was seen in single cells (f, inset), within groups of cells or in concentrated extracellular areas within the brain parenchyma, or close to blood vessels (e and d, arrows). The presence of the sAPPα transgene was confirmed by immunocytochemistry using 6E10 (g-i) and showed a similar localization pattern to that detected with GFP immunocytochemistry. Panels b and d show the absence of immunoreactivity in representative sections treated without the addition of primary (1°) antibody.

We next extended our investigations by injecting untransfected MAPCs obtained from the donor marrow of EGFP expressing mice or donor MAPCs transfected with human sAPPα ($1 \times 10^6$/50 μl per mouse) into recipient nontransgenic (nonTg) mice or PS/APP transgenic mice (FIG. 5). Untransfected MAPCS (n=3 mice for each genotype) or transfected MAPCs (n=3 mice for each genotype) were administered by intravenous tail vein injection. Immunohistochemical examination was performed on all mice using antibodies to GFP, to detect all MAPC donor cells, and with 6E10, to detect MAPCs transfected with sAPPα. Six weeks after injection, immunocytochemical analyses showed the presence of MAPCs within the brain parenchyma of PS/APP mice and nonTg control mice (FIG. 5). Untransfected MAPCs and MAPCs transfected with sAPPα showed similar distribution patterns. Notably, the injected cells were localized predominantly around the cerebral blood vessels (FIG. 5). At 8 weeks postinjection of MAPCs, immunoreactivity detected with either GFP or 6E10 antibodies was found deep within the brain parenchyma and displayed several distribution patterns: confined to the abluminal side of the cerebral vasculature, within few single cells within the brain parenchyma, or, most predominantly, within relatively confined extracellular areas throughout the brain parenchyma (FIG. 5). No immunoreactivity was observed within tissue sections from the brains of transgenic PS/APP or nonTg mice incubated in the absence of primary antibodies.

Example 2

Intranasal Administration of MAPCs

To examine whether MAPCs could be delivered to brain via an intranasal route, undifferentiated marrow derived adult progenitor cells (MAPCs) were isolated and expanded as previously described (Chen et al., Curr Alz Res 3: 63-70 (2006)). Nine mice receiving one unilateral cortical or striatal stab lesion were given MAPCs administered intranasally under mild anesthesia following recovery from surgery. Each mouse received one 10 µL volume of 0.9% saline containing 25,000 cells into each of the nares. The cells were administered dropwise with a pipette and gel-loading tip. The control group of lesioned animals received 10 µL of sterile 0.9% saline within each nostril. Non-lesioned animals were given either intranasal MAPCs or sterile saline.

All animals were sacrificed by transcardiac perfusion with aldehydes at 3 or 24 hrs, and 3, 7, or 14 day time intervals following MAPC administration and 40 µm thick vibratome sections were cut in the sagittal plane taking care to preserve the olfactory bulbs. The identity of MAPCs was confirmed by immunocytochemistry and negative staining with the hematopoietic cell marker, CD45 (Santa Cruz Biotechnology, Inc., Santa Cruz Calif.). The presence of green fluorescent protein (GFP) positive cells was confirmed using fluorescence microscopy. In addition, immunocytochemical analyses were performed using a primary antibody to GFP (Santa Cruz Biotechnology, Inc., Santa Cruz Calif.) and diaminobenzidine immunocytochemistry (Vector Laboratories, Burlingame Calif.) to further confirm the presence of MAPCs in tissue. Double label immunofluorescence microscopy for several markers characteristic of neuronal and glial cells was used to determine the stage of MAPC development. These included antibodies to the neural progenitor stage marker, nestin (Santa Cruz Biotechnology, Inc., Santa Cruz Calif.,) and markers for differentiated glia and neurons: glial fibrillary acidic protein (GFAP; DAKO Corporation, Carpinteria Calif.), neuron-specific nuclear protein (NeuN; Upstate/Chemicon Temecula, Calif.) and synaptophysin (Syn; Santa Cruz Biotechnology, Inc., Santa Cruz Calif.).

Figure 6:
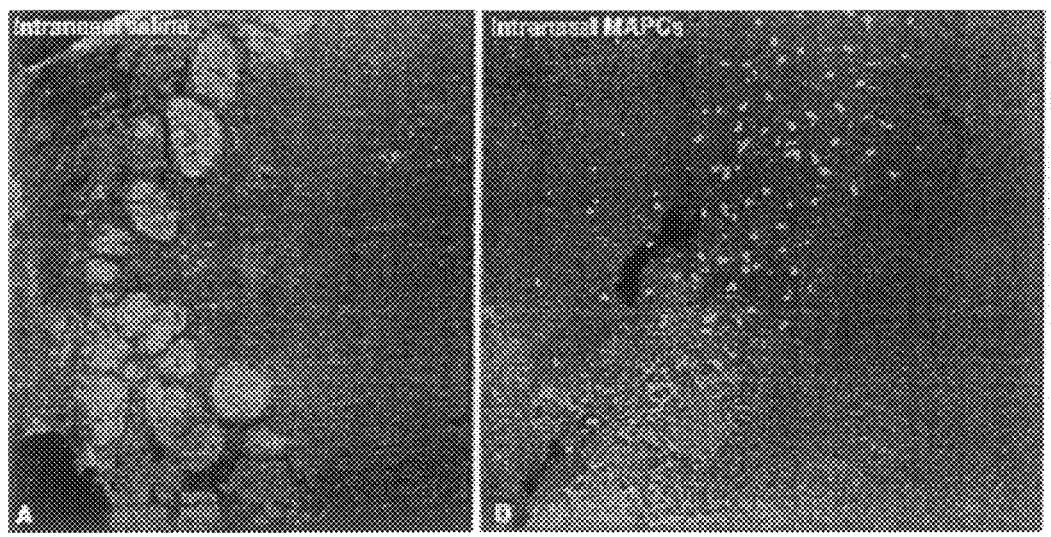
FIG. 6. is a photomicrograph showing intranasal administration of MAPCs. Mice receiving intranasal saline only (A), show no evidence of endogenous GFP fluorescence within the glomerular layer. However, animals receiving donor GFP-positive MAPCs by intranasal (i.n.) administration exhibited numerous fluorescent cells within glomerular layer of the olfactory bulb (OB) (B), suggesting the influx of these cells by a transnasal route.
Figure 7:
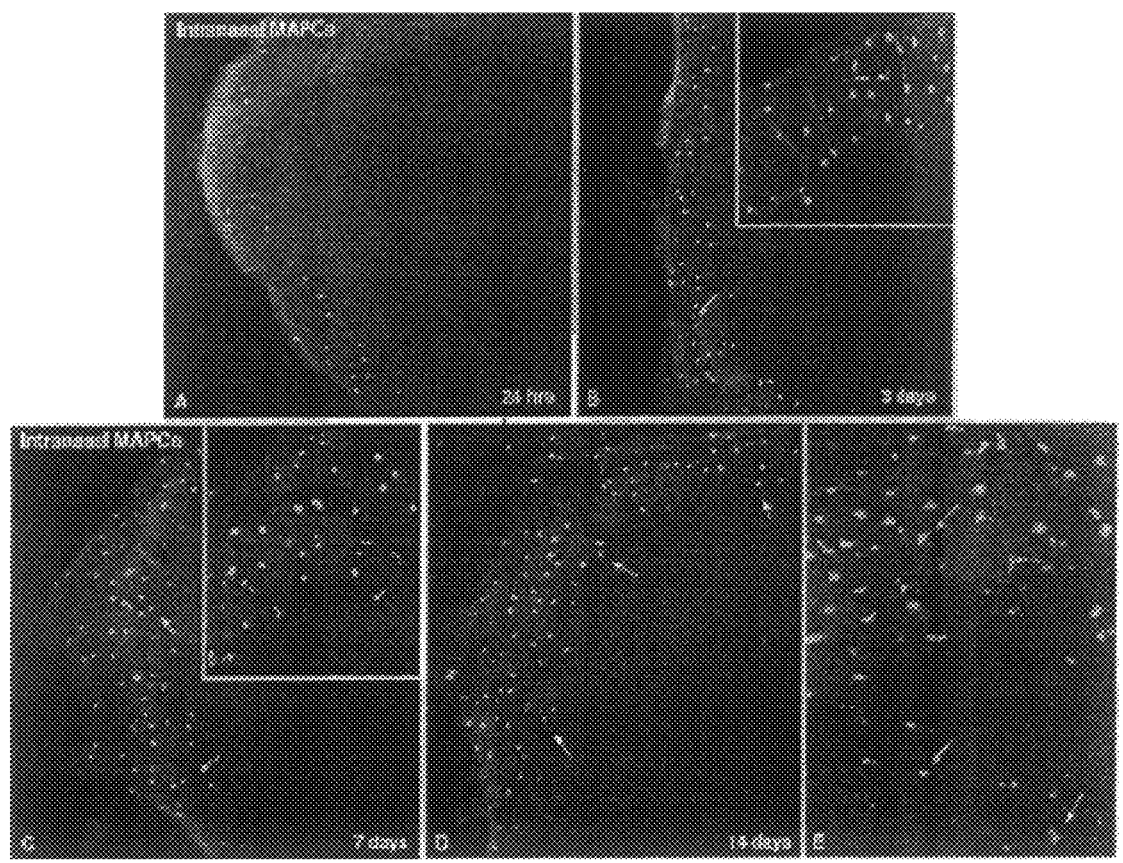
FIG. 7. is a photomicrograph showing that MAPCs migrate within the olfactory bulb following intranasal delivery. Twenty four hrs after intranasal administration of GFP-positive MAPCs, stem cells infiltrated the olfactory bulb of unlesioned mice where they appeared within the nerve and glomerular cell layers (A). By 3 days post-treatment, MAPCs were localized predominantly within the glomerular cell layer and often observed between individual glomerular tufts (B, B inset, arrows). GFP-positive MAPCs flooded the glomerular cell layer at both 7 (C, C inset arrows) and 14 (D, arrows) days post intranasal delivery of cells and remained within the glomerular and external plexiform layers. Few GFP-positive cells were seen within the intermediate zone 14 days following intranasal administration (E, arrows).

Unlesioned mice and mice receiving a single unilateral cortical or striatal stab lesion received one intranasal dose (50,000 cells/20 µl) of GFP-positive MAPCs and were sacrificed at 3 hrs and 1, 3, 7, and 14 days following MAPC administration. An equal number of mice received saline intranasally and served as controls. Prior to nasal administration, immunocytochemistry using CD45, the neuronal marker, NeuN, and the astroglial marker, GFAP, was used to confirm that GFP-positive MAPCs obtained from donor mice were devoid of neuronal and glial specific antigens. Vibratome sections from the saline and MAPC treated groups were examined for the presence of GFP-positive cells by fluorescence microscopy as well as by immunocytochemistry using an antibody to GFP at each timepoint. In sagittal, 40 mm thick sections from unlesioned mice, GFP-positive MAPCs were visible within the nerve and glomerular cell layers of the olfactory bulb within 24 hours post intranasal administration (FIGS. 6 and 7A). Three to seven days post intranasal dosing with MAPCs, the majority of GFP-positive MAPCs were visible within the glomerular cell layer (FIGS. 7B and C). By fourteen days following intranasal delivery of MAPCs, GFP-positive cells were detected predominantly within the glomerular cell layer. Rare MAPCs were seen within the intermediate superficial zone (FIGS. 7D and E). The presence of GFP-positive MAPCs delivered by intranasal administration was also confirmed using antibodies to GFP. Serial adjacent, 1 mm thick sections obtained from GFP immunostained tissue and counterstained with toluidine blue showed the typical topography of the glomerular cell layer and the prominent appearance of basal periglomerular cells. Few GFP-immunoreactive MAPCs were observed within the intermediate superficial zone between the glomerular cell layer and the mitral/tufted cell layer. Mice given intranasal saline, in contrast to those given GFP-positive MAPCs, did not express GFP and showed no evidence of GFP fluorescence (FIG. 6).

Figure 8:
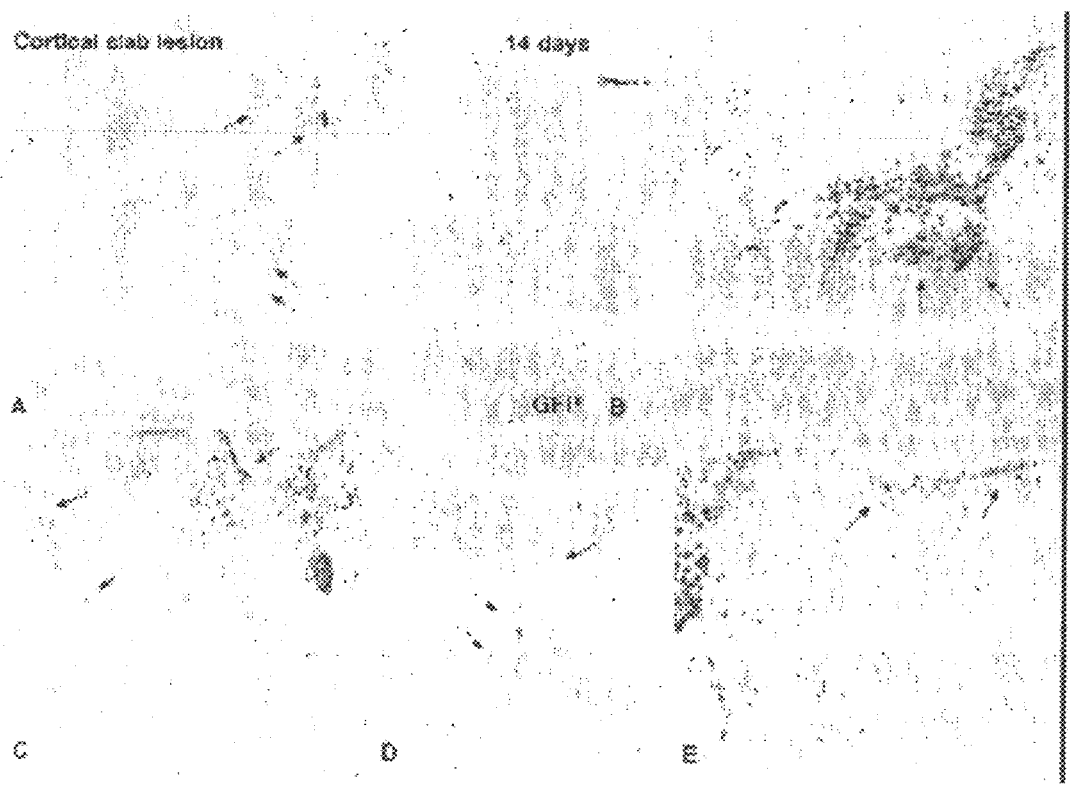
FIG. 8. is a photomicrograph showing the distribution of donor GFP-positive MAPCs in the brains of lesioned mice. Following i.n. delivery of GFP-positive MAPCs, immunocytochemistry using GFP antibodies revealed intensely positive cells infiltrating the proximal portions (A and B, arrows) and needle tract (A and D, arrows) of mice receiving cortical stab lesions. Immunoreactive cells were also associated with the regional vasculature (C and E, arrows) close to the site of the lesion.

The ability of MAPCs to undergo site-specific migration has been reported in a number of previous studies (see Brazelton et al., 2000; Gage, 2000, Jiang et al., 2000; Mezey et al., 2000 Verfaille et al., 2003; Woodbury et al. 2000 for additional references). In brain tissue damaged by mechanical or chemical lesions, MAPCs injected into the injured brain area migrate and engraft to compromised regions (Hellmann et al., 2006; Honma et al., 2006; Li et al., 2001; Lu et al., 2001; Willing et al., 2003) and have been shown to survive better in damaged hemispheres compared to unlesioned contralateral hemispheres. We addressed the question of whether damage to the cortex or striatum may enhance intranasal MAPCs delivery to brain and more specifically to the lesioned site. Mice were given mechanical stab lesions to the cortex or striatum and were dosed intranasally with GFP-positive MAPCs as described above. As early as 3 hours and within 24 hours post administration, the majority of GFP-positive MAPCs were concentrated predominantly within the glomerular layer of the olfactory bulb. By 3 to 7 days, GFP-positive MAPCs were concentrated within the glomerular layer as well as on the distal/outer aspects of the glomerular cell layer. A modest number of GFP-positive MAPCs were also present within intermediate superficial zone between the external and the internal plexiform layers. However, MAPCs were not seen within the mitral/tufted cell layer (data not shown). Immunocytochemical analyses of lesioned brains examined 3 days following MAPC dosing using anti-GFP antibodies similarly revealed the presence of donor GFP-positive MAPCs throughout the olfactory bulb and at the lesion site (FIG. 3) including the pial surface in close proximity to the lesion (FIG. 8). By 2 weeks post intranasal delivery of stem cells, MAPCs were associated with both proximal and distal borders of the lesion site. Lateral movement of moderate numbers of MAPCs toward the distal portion of the lesion was quite dramatic (FIG. 8). Examination of the livers from lesioned and unlesioned mice showed greater numbers of GFP-positive MAPCs in the unlesioned mice compared to lesioned animals, suggesting that tissue damage not only enhanced the migration, but reduced the clearance and promoted a longer survival of donor MAPCs in brain.

We next sought to examine if GFP-positive MAPCs administered intranasally and which had entered the brain could develop into neurons that express neuronal specific antigens, supporting the idea that MAPCs have the potential to differentiate into cells of neural lineage and, possibly, even functional neurons. Similar to the GFP fluorescence, immunocytochemical analyses of GFP-positive MAPCs that had migrated into the area of the lesion revealed that these cells were CD45-negative and nestin-positive (data not shown). At four to six weeks after MAPC delivery, our initial findings using double label immunocytochemistry showed that many GFP-positive MAPCs in these areas had differentiated into cells that expressed weak immunoreactivity for nestin but strong immunostaining with several neuron-specific markers, such as NeuN and synapotophysin (data not shown). Rare GFP-positive MAPCs were GFAPpositive (data not shown).

The numbers of GFP-positive MAPCs within the olfactory bulb and deeper brain was increased in mice receiving cortical or striatal lesions, in contrast to unlesioned mice, suggesting that injury contributes to the accelerated entry and migration of MAPCs. Specifically, our examination by fluorescent and immunocytochemical analyses twenty-four hours after delivery of intranasal MAPCs showed that increased numbers of GFP-positive cells were present within the glomerular layer of lesioned mice compared to unlesioned animals, with deeper migration into brain and the site of injury by 1 to 2 weeks in lesioned animals.

Sequence Appendix

The following Sequence Appendix includes the nucleic acid sequence for human sAPPα (SEQ ID NO:1) and the alignment of several sAPPα xenologues with human sAPPα.

In each case, human sAPPα is the query sequence and the subject (sbjct) sequence is the corresponding sequence from the indicated species. Conserved nucleic acid residues are indicated by a dot (.) and residues which are not conserved are indicated by a substituted residue. Percent identity between the indicated species and humans is also indicated.

```
                                Sequence Appendix

SEQ ID NO: 1
Human sAPPα
    1 atgctgcccg gtttggcact gctcctgctg gccgcctgga cggctcgggc gctggaggta 61 cccactgatg gtaatgctgg cctgctggct gaaccccaga ttgccatgtt ctgtggcaga 121 ctgaacatgc acatgaatgt ccagaatggg aagtgggatt cagatccatc agggaccaaa 181 acctgcattg ataccaagga aggcatcctg cagtattgcc aagaagtcta ccctgaactg 241 cagatcacca atgtggtaga agccaaccaa ccagtgacca tccagaactg gtgcaagcgg 301 ggccgcaagc agtgcaagac ccatccccac tttgtgattc cctaccgctg cttagttggt 361 gagtttgtaa gtgatgccct tctcgttcct gacaagtgca aattcttaca ccaggagagg 421 atggatgttt gcgaaactca tcttcactgg cacaccgtcg ccaaagagac atgcagtgag 481 aagagtacca acttgcatga ctacggcatg ttgctgccct gcggaattga caagttccga 541 ggggtagagt ttgtgtgttg cccactggct gaagaaagtg acaatgtgga ttctgctgat 601 gcggaggagg atgactcgga tgtctggtgg ggcggagcag acacagacta tgcagatggg 661 agtgaagaca aagtagtaga agtagcagag gaggaagaag tggctgaggt ggaagaagaa 721 gaagccgatg atgacgagga cgatgaggat ggtgatgagg tagaggaaga ggctgaggaa 781 ccctacgaag aagccacaga gagaaccacc agcattgcca ccaccaccac caccaccaca 841 gagtctgtgg aagaggtggt tcgagttcct acaacagcag ccagtacccc tgatgccgtt 901 gacaagtatc tcgagacacc tggggatgag aatgaacatg cccatttcca gaaagccaaa 961 gagaggcttg aggccaagca ccgagagaga atgtcccagg tcatgagaga atgggaagag 1021 gcagaacgtc aagcaaagaa cttgcctaaa gctgataaga aggcagttat ccagcatttc 1081 caggagaaag tggaatcttt ggaacaggaa gcagccaacg agagacagca gctggtggag 1141 acacacatgg ccagagtgga agccatgctc aatgaccgcc gccgcctggc cctggagaac 1201 tacatcaccg ctctgcaggc tgttcctcct cggcctcgtc acgtgttcaa tatgctaaag 1261 aagtatgtcc gcgcagaaca gaaggacaga cagcacaccc taaagcattt cgagcatgtg 1321 cgcatggtgg atcccaagaa agccgctcag atccggtccc aggttatgac acacctccgt 1381 gtgatttatg agcgcatgaa tcagtctctc tccctgctct acaacgtgcc tgcagtggcc 1441 gaggagattc aggatgaagt tgatgagctg cttcagaaag agcaaaacta ttcagatgac 1501 gtcttggcca acatgattag tgaaccaagg atcagttacg gaaacgatgc tctcatgcca 1561 tctttgaccg aaacgaaaac caccgtggag ctccttcccg tgaatggaga gttcagcctg 1621 gacgatctcc agccgtggca ttctttggg gctgactctg tgccagccaa cacagaaaac 1681 gaagttgagc ctgttgatgc ccgccctgct gccgaccgag gactgaccac tcgaccaggt 1741 tctgggttga caaatatcaa gacggaggag atctctgaag tgaagatgga tgcagaattc 1801 cgacatgact caggatatga agttcatcat caaaaattgg tgttctttgc agaagatgtg 1861 ggttcaaaca aaggtgcaat cattggactc atggtgggcg gtgttgtcat agcgacagtg 1921 atcgtcatca ccttggtgat gctgaagaag aaacagtaca catccattca tcatggtgtg
```

Sequence Appendix

```
1981 gtggaggttg acgccgctgt cacccagag gagcgccacc tgtccaagat gcagcagaac 2041 ggctacgaaa atccaaccta caagttcttt gagcagatgc agaactag SEQ ID NO: 2
CHIMPANZEE
>gi|61316398|ref|NM_001013018.1| Pan troglodytes (CHIMPANZEE) amyloid beta
A4 protein (APP), mRNA
Length = 2313
Score = 1909 bits (963), Expect = 0.0
Identities = 969/971 (99%), Gaps = 0/971 (0%)
Strand = Plus/Plus Query  866  TTCCTACAACAGCAGCCAGTACCCCTGATGCCGTTGACAAGTATCTCGAGACACCTGGGG   925
Sbjct 1091  ............................................................  1150

Query  926  ATGAGAATGAACATGCCCATTTCCAGAAAGCCAAAGAGAGGCTTGAGGCCAAGCACCGAG   985
Sbjct 1151  ............................................................  1210

Query  986  AGAGAATGTCCCAGGTCATGAGAGAATGGGAAGAGGCAGAACGTCAAGCAAAGAACTTGC  1045
Sbjct 1211  ............................................................  1270

Query 1046  CTAAAGCTGATAAGAAGGCAGTTATCCAGCATTTCCAGGAGAAAGTGGAATCTTTGGAAC  1105
Sbjct 1271  ............................................................  1330

Query 1106  AGGAAGCAGCCAACGAGAGACAGCAGCTGGTGGAGACACACATGGCCAGAGTGGAAGCCA  1165
Sbjct 1331  ............................................................  1390

Query 1166  TGCTCAATGACCGCCGCCGCCTGGCCCTGGAGAACTACATCACCGCTCTGCAGGCTGTTC  1225
Sbjct 1391  ............................................................  1450

Query 1226  CTCCTCGGCCTCGTCACGTGTTCAATATGCTAAAGAAGTATGTCCGCGCAGAACAGAAGG  1285
Sbjct 1451  ............................................................  1510

Query 1286  ACAGACAGCACACCCTAAAGCATTTCGAGCATGTGCGCATGGTGGATCCCAAGAAAGCCG  1345
Sbjct 1511  ...........................................................T.  1570

Query 1346  CTCAGATCCGGTCCCAGGTTATGACACACCTCCGTGTGATTTATGAGCGCATGAATCAGT  1405
Sbjct 1571  .........................................C.................  1630

Query 1406  CTCTCTCCCTGCTCTACAACGTGCCTGCAGTGGCCGAGGAGATTCAGGATGAAGTTGATG  1465
Sbjct 1631  ............................................................  1690

Query 1466  AGCTGCTTCAGAAAGAGCAAAACTATTCAGATGACGTCTTGGCCAACATGATTAGTGAAC  1525
Sbjct 1691  ............................................................  1750

Query 1526  CAAGGATCAGTTACGGAAACGATGCTCTCATGCCATCTTTGACCGAAACGAAAACCACCG  1585
Sbjct 1751  ............................................................  1810

Query 1586  TGGAGCTCCTTCCCGTGAATGGAGAGTTCAGCCTGGACGATCTCCAGCCGTGGCATTCTT  1645
Sbjct 1811  ............................................................  1870

Query 1646  TTGGGGCTGACTCTGTGCCAGCCAACACAGAAAACGAAGTTGAGCCTGTTGATGCCCGCC  1705
Sbjct 1871  ............................................................  1930

Query 1706  CTGCTGCCGACCGAGGACTGACCACTCGACCAGGTTCTGGGTTGACAAATATCAAGACGG  1765
Sbjct 1931  ............................................................  1990

Query 1766  AGGAGATCTCTGAAGTGAAGATGGATGCAGAATTCCGACATGACTCAGGATATGAAGTTC  1825
Sbjct 1991  ............................................................  2050

Query 1826  ATCATCAAAAA                                                  1836
Sbjct 2051  ...........                                                  2061

SEQ ID NO: 3
Score = 1604 bits (809), Expect = 0.0
Identities = 815/817 (99%), Gaps = 0/817 (0%)
Strand = Plus/Plus Query    1  ATGCTGCCCGGTTTGGCACTGCTCCTGCTGGCCGCCTGGACGGCTCGGGCGCTGGAGGTA    60
Sbjct    1  ...............G............................................    60

Query   61  CCCACTGATGGTAATGCTGGCCTGCTGGCTGAACCCCAGATTGCCATGTTCTGTGGCAGA   120
Sbjct   61  ............................................................   120

Query  121  CTGAACATGCACATGAATGTCCAGAATGGGAAGTGGGATTCAGATCCATCAGGGACCAAA   180
Sbjct  121  ............................................................   180
```

| Sequence Appendix |
|---|

```
Query  181  ACCTGCATTGATACCAAGGAAGGCATCCTGCAGTATTGCCAAGAAGTCTACCCTGAACTG  240
Sbjct  181  ............................................................  240

Query  241  CAGATCACCAATGTGGTAGAAGCCAACCAACCAGTGACCATCCAGAACTGGTGCAAGCGG  300
Sbjct  241  ............................................................  300

Query  301  GGCCGCAAGCAGTGCAAGACCCATCCCCACTTTGTGATTCCCTACCGCTGCTTAGTTGGT  360
Sbjct  301  ............................................................  360

Query  361  GAGTTTGTAAGTGATGCCCTTCTCGTTCCTGACAAGTGCAAATTCTTACACCAGGAGAGG  420
Sbjct  361  ............................................................  420

Query  421  ATGGATGTTTGCGAAACTCATCTTCACTGGCACACCGTCGCCAAAGAGACATGCAGTGAG  480
Sbjct  421  ...........T................................................  480

Query  481  AAGAGTACCAACTTGCATGACTACGGCATGTTGCTGCCCTGCGGAATTGACAAGTTCCGA  540
Sbjct  481  ............................................................  540

Query  541  GGGGTAGAGTTTGTGTGTTGCCCACTGGCTGAAGAAAGTGACAATGTGGATTCTGCTGAT  600
Sbjct  541  ............................................................  600

Query  601  GCGGAGGAGGATGACTCGGATGTCTGGTGGGCGGAGCAGACACAGACTATGCAGATGGG   660
Sbjct  601  ............................................................  660

Query  661  AGTGAAGACAAAGTAGTAGAAGTAGCAGAGGAGGAAGAAGTGGCTGAGGTGGAAGAAGAA  720
Sbjct  661  ............................................................  720

Query  721  GAAGCCGATGATGACGAGGACGATGAGGATGGTGATGAGGTAGAGGAAGAGGGTGAGGAA  780
Sbjct  721  ............................................................  780

Query  781  CCCTACGAAGAAGCCACAGAGAGAACCACCAGCATTG                        817
Sbjct  781  .....................................                        817

SEQ ID NO: 4
Score = 52.0 bits (26), Expect = 0.007
Identities = 26/26 (100%), Gaps = 0/26 (0%)
Strand = Plus/Plus Query  840  AGAGTCTGTGGAAGAGGTGGTTCGAG                                    865
Sbjct  840  ..........................                                    865

SEQ ID NO: 5
ORANGUTAN
>gi|55733522|emb|CR861380.1| Pongo pygmaeus (ORANGUTAN) mRNA; cDNA
DKFZp459D212 (from clone DKFZp459D212)
Length = 3079

Score = 1889 bits (953), Expect = 0.0
Identities = 986/997 (98%), Gaps = 0/997 (0%)
Strand = Plus/Plus Query  840   AGAGTCTGTGGAAGAGGTGGTTCGAGTTCCTACAACAGCAGCCAGTACCCCTGATGCCGT  899
Sbjct  952   ............................................................  1011

Query  900   TGACAAGTATCTCGAGACACCTGGGGATGAGAATGAACATGCCCATTTCCAGAAAGCCAA  959
Sbjct  1012  ..............................................C.............  1071

Query  960   AGAGAGGCTTGAGGCCAAGCACCGAGAGAGAATGTCCCAGGTCATGAGAGAATGGGAAGA  1019
Sbjct  1072  ............................................................  1131

Query  1020  GGCAGAACGTCAAGCAAAGAACTTGCCTAAAGCTGATAAGAAGGCAGTTATCCAGCATTT  1079
Sbjct  1132  ............................................................  1191

Query  1080  CCAGGAGAAAGTGGAATCTTTGGAACAGGAAGCAGCCAACGAGAGACAGCAGCTGGTGGA  1139
Sbjct  1192  ............................................................  1251

Query  1140  GACACACATGGCCAGAGTGGAAGCCATGCTCAATGACCGCCGCCGCCTGGCCCTGGAGAA  1199
Sbjct  1252  ............................................................  1311

Query  1200  CTACATCACCGCTCTGCAGGCTGTTCCTCCTCGGCCTCGTCACGTGTTCAATATGCTAAA  1259
Sbjct  1312  ............................................................  1371

Query  1260  GAAGTATGTCCGCGCAGAACAGAAGGACAGACAGCACACCCTAAAGCATTTCGAGCATGT  1319
Sbjct  1372  ............................................................  1431

Query  1320  GCGCATGGTGGATCCCAAGAAAGCCGCTCAGATCCGGTCCCAGGTTATGACACACCTCCG  1379
Sbjct  1432  ................................T...........................  1491
```

Sequence Appendix

```
Query  1380  TGTGATTTATGAGCGCATGAATCAGTCTCTCTCCCTGCTCTACAACGTGCCTGCAGTGGC  1439
Sbjct  1492  .........C..................................................  1551

Query  1440  CGAGGAGATTCAGGATGAAGTTGATGAGCTGCTTCAGAAAGAGCAAAACTATTCAGATGA  1499
Sbjct  1552  ............................................................  1611

Query  1500  CGTCTTGGCCAACATGATTAGTGAACCAAGGATCAGTTACGGAAACGATGCTCTCATGCC  1559
Sbjct  1612  ......................................................A..C.......  1671

Query  1560  ATCTTTGACCGAAACGAAAACCACCGTGGAGCTCCTTCCCGTGAATGGAGAGTTCAGCCT  1619
Sbjct  1672  G.....................................T.....T..................  1731

Query  1620  GGACGATCTCCAGCCGTGGCATTCTTTTGGGGCTGACTCTGTGCCAGCCAACACAGAAAA  1679
Sbjct  1732  ............................................................  1791

Query  1680  CGAAGTTGAGCCTGTTGATGCCCGCCCTGCTGCCGACCGAGGACTGACCACTCGACCAGG  1739
Sbjct  1792  ...................T.................G.....................  1851

Query  1740  TTCTGGGTTGACAAATATCAAGACGGAGGAGATCTCTGAAGTGAAGATGGATGCAGAATT  1799
Sbjct  1852  ............................................................  1911

Query  1800  CCGACATGACTCAGGATATGAAGTTCATCATCAAAAA  1836
Sbjct  1912  ..........G..........................  1948

SEQ ID NO: 6
Score = 1513 bits (763), Expect = 0.0
Identities = 802/815 (98%), Gaps = 0/815 (0%)
Strand = Plus/Plus Query    1  ATGCTGCCCGGTTTGGCACTGCTCCTGCTGGCCGCCTGGACGGCTCGGGCGCTGGAGGTA    60
Sbjct  113  ............................................................   172

Query   61  CCCACTGATGGTAATGCTGGCCTGCTGGCTGAACCCCAGATTGCCATGTTCTGTGGCAGA   120
Sbjct  173  ..........C.................................................   232

Query  121  CTGAACATGCACATGAATGTCCAGAATGGGAAGTGGGATTCAGATCCATCAGGGACCAAA   180
Sbjct  233  ............................................................   292

Query  181  ACCTGCATTGATACCAAGGAAGGCATCCTGCAGTATTGCCAAGAAGTCTACCCTGAACTG   240
Sbjct  293  ............................................................   352

Query  241  CAGATCACCAATGTGGTAGAAGCCAACCAACCAGTGACCATCCAGAACTGGTGCAAGCGG   300
Sbjct  353  ............................................................   412

Query  301  GGCCGCAAGCAGTGCAAGACCCATCCCCACTTTGTGATTCCCTACCGCTGCTTAGTTGGT   360
Sbjct  413  ............................................................   472

Query  361  GAGTTTGTAAGTGATGCCCTTCTCGTTCCTGACAAGTGCAAATTCTTACACCAGGAGAGG   420
Sbjct  473  ..A........C..............................G............   532

Query  421  ATGGATGTTTGCGAAACTCATCTTCACTGGCACACCGTCGCCAAAGAGACATGCAGTGAG   480
Sbjct  533  ...........T..................................G.........   592

Query  481  AAGAGTACCAACTTGCATGACTACGGCATGTTGCTGCCCTGCGGAATTGACAAGTTCCGA   540
Sbjct  593  ............................................................   652

Query  541  GGGGTAGAGTTTGTGTGTTGCCCCACTGGCTGAAGAAAGTGACAATGTGGATTCTGCTGAT   600
Sbjct  653  ................................G........................C   712

Query  601  GCGGAGGAGGATGACTCGGATGTCTGGTGGGGCGGAGCAGACACAGACTATGCAGATGGG   660
Sbjct  713  ............................................................   772

Query  661  AGTGAAGACAAAGTAGTAGAAGTAGCAGAGGAGGAAGAAGTGGCTGAGGTGGAAGAAGAA   720
Sbjct  773  ............................................................   832

Query  721  GAAGCCGATGATGACGAGGACGATGAGGATGGTGATGAGGTAGAGGAAGAGGCTGAGGAA   780
Sbjct  833  .....TC..........T..............C..........................   892

Query  781  CCCTACGAAGAAGCCACAGAGAGAACCACCAGCAT   815
Sbjct  893  .......G...........................   927
```

SEQ ID NO: 7
LONG-TAILED MACAQUE
>gi|342062|gb|M58727.1|MACABPKPIB *M. fascicularis* (LONG-TAILED MACAQUE) amyloid b-protein precursor mRNA,
complete cds
Length = 3098

-continued

Sequence Appendix

```
Score = 1816 bits (916), Expect = 0.0
Identities = 976/996 (97%), Gaps = 0/996 (0%)
Strand = Plus/Plus Query    841 GAGTCTGTGGAAGAGGTGGTTCGAGTTCCTACAACAGCAGCCAGTACCCCTGATGCCGTT    900
Sbjct    984 ............................................................   1043

Query    901 GACAAGTATCTCGAGACACCTGGGGATGAGAATGAACATGCCCATTTCGACAAAGCCAAA    960
Sbjct   1044 ........C..T.......................C........................   1103

Query    961 GAGAGGCTTGAGGCCAAGCACCGAGAGAGAATGTCCCAGGTCATGAGAGAATGGGAAGAG   1020
Sbjct   1104 .....A......................................................   1163

Query   1021 GCAGAACGTCAAGCAAAGAACTTGCCTAAAGCTGATAAGAAGGCAGTTATCCAGCATTTC   1080
Sbjct   1164 ...........G.................................................   1223

Query   1081 CAGGAGAAAGTGGAATCTTTGGAACAGGAAGCAGCCAACGAGAGACAGCAGCTGGTGGAG   1140
Sbjct   1224 .............................................................   1283

Query   1141 ACACACATGGCCAGAGTGGAAGCCATGCTCAATGACCGCCGCCGCCTGGCCCTGGAGAAC   1200
Sbjct   1284 .............................................................   1343

Query   1201 TACATCACCGCTCTGCAGGCTGTTCCTCCTCGGCCTCGTCACGTGTTCAATATGCTAAAG   1260
Sbjct   1344 ........T..........C...........................G...          1403

Query   1261 AAGTATGTCCGCGCAGAACAGAAGGACAGACAGCACACCCTAAAGCATTTCGAGCATGTG   1320
Sbjct   1404 .....C.........................G.................A          1463

Query   1321 CGCATGGTGGATCCCAAGAAAGCCGCTCAGATCCGGTCCCAGGTTATGACACACCTCCGT   1380
Sbjct   1464 ................T............................................   1523

Query   1381 GTGATTTATGAGCGCATGAATCAGTCTCTCTCCCTGCTCTACAACGTGCCTGCAGTGGCC   1440
Sbjct   1524 ........C...........C........................................   1583

Query   1441 GAGGAGATTCAGGATGAAGTTGATGAGCTGCTTCAGAAAGAGCAAAACTATTCAGATGAC   1500
Sbjct   1584 .............................................................   1643

Query   1501 GTCTTGGCCAACATGATTAGTGAACCAAGGATCAGTTACGGAAACGATGCTCTCATGCCA   1560
Sbjct   1644 ..........................................................G    1703

Query   1561 TCTTTGACCGAAACGAAAACCACCGTGGAGCTCCTTCCCGTGAATGGAGAGTTCAGCCTG   1620
Sbjct   1704 .............T........T......................................   1763

Query   1621 GACGATCTCCAGCCGTGGCATTCTTTTGGGGCTGACTCTGTGCCAGCCAACACAGAAAAC   1680
Sbjct   1764 ................................C............................   1823

Query   1681 GAAGTTGAGCCTGTTGATGCCCGCCCTGCTGCCGACCGAGGACTGACCACTCGACCAGGT   1740
Sbjct   1824 .............................................................   1883

Query   1741 TCTGGGTTGACAAATATCAAGACGGAGGAGATCTCTGAAGTGAAGATGGATGCAGAATTC   1800
Sbjct   1884 ......................A......................................   1943

Query   1801 CGACATGACTCAGGATATGAAGTTCATCATCAAAAA                          1836
Sbjct   1944 ..............T.....................                          1979

SEQ ID NO: 8
Score = 1505 bits (759), Expect = 0.0
Identities = 801/815 (98%), Gaps = 0/815 (0%)
Strand = Plus/Plus Query      1 ATGCTGCCCGGTTTGGCACTGCTCCTGCTGGCCGCCTGGACGGCTCGGGCGCTGGAGGTA     60
Sbjct    144 .............................................................    203

Query     61 CCCACTGATGGTAATGCTGGCCTGCTGGCTGAACCCCAGATTGCCATGTTCTGTGGCAGA    120
Sbjct    204 ..T.....C.........................C.........................    263

Query    121 CTGAACATGCACATGAATGTCCAGAATGGGAAGTGGGATTCAGATCCATCAGGGACCAAA    180
Sbjct    264 .............................................................    323

Query    181 ACCTGCATTGATACCAAGGAAGGCATCCTGCAGTATTGCCAAGAAGTCTACCCTGAACTG    240
Sbjct    324 .............................................................    383

Query    241 CAGATCACCAATGTGGTAGAAGCCAACCAACCAGTGACCATCCAGAACTGGTGCAAGCGG    300
Sbjct    384 .........................................................A..    443

Query    301 GGCCGCAAGCAGTGCAAGACCCATCCCCACTTTGTGATTCCCTACCGCTGCTTAGTTGGT    360
Sbjct    444 ...........................................T.........          503
```

Sequence Appendix

```
Query  361  GAGTTTGTAAGTGATGCCCTTCTCGTTCCTGACAAGTGCAAATTCTTACACCAGGAGAGG  420
Sbjct  504  .........C..................................................  563

Query  421  ATGGATGTTTGCGAAACTCATCTTCACTGGCACACCGTCGCCAAAGAGACATGCAGTGAG  480
Sbjct  564  .....................................................G........  623

Query  481  AAGAGTACCAACTTGCATGACTACGGCATGTTGCTGCCCTGCGGAATTGACAAGTTCCGA  540
Sbjct  624  .....C.........................T.....C..T..  683

Query  541  GGGGTAGAGTTTGTGTGTTGCCCACTGGCTGAAGAAAGTGACAATGTGGATTCTGCTGAT  600
Sbjct  684  ........................G...................................  743

Query  601  GCGGAGGAGGATGACTCGGATGTCTGGTGGGCGCCAGCAGACACAGACTATGCAGATGGG  660
Sbjct  744  ..........................................................C...  803

Query  661  AGTGAAGACAAAGTAGTAGAAGTAGCAGAGGAGGAAGAAGTGGCTGAGGTGGAAGAAGAA  720
Sbjct  804  ..........................................C.................  863

Query  721  GAAGCCGATGATGACGAGGACGATGAGGATGGTGATGAGGTAGAGGAAGAGGCTGAGGAA  780
Sbjct  864  ............................................................  923

Query  781  CCCTACGAAGAAGCCACAGAGAGAACCACCAGCAT                            815
Sbjct  924  ...................................                            958

SEQ ID NO: 9
MOUSE
>gi|47271503|ref|NM_007471.2| Mus musculus (MOUSE) amyloid beta
(A4) precursor protein (App), mRNA
Length = 3140

Score = 1166 bits (588), Expect = 0.0
Identities = 894/996 (89%), Gaps = 0/996 (0%)
Strand = Plus/Plus Query  841  GAGTCTGTGGAAGAGGTGGTTCGAGTTCCTACAACAGCAGCCAGTACGCCTCATGCCGTT   900
Sbjct  986  .....C.....G........C........C..G...........C.....C..C.....C  1045

Query  901  GACAAGTATCTCGAGACACCTGGGGATGAGAATGAACATGCCCATTTCCAGAAAGCCAAA   960
Sbjct 1046  ........C..G........C.....C.....C..G........................  1105

Query  961  GAGAGGCTTGAGGCCAAGCACCGAGAGAGAATGTCCCAGGTCATGAGAGAATGGGAAGAG  1020
Sbjct 1106  ........G..A................................................  1165

Query 1021  GCAGAACGTCAAGCAAAGAACTTGCCTAAAGCTGATAAGAAGGCAGTTATCCAGCATTTC  1080
Sbjct 1166  .....G........C........C........C........C.................  1225

Query 1081  CAGGAGAAAGTGGAATCTTTGGAACAGGAAGCAGCCAACGAGAGACAGCAGCTGGTGGAG  1140
Sbjct 1226  ...............C....................T...............T..A...  1285

Query 1141  ACACACATGGCCAGAGTGGAAGCCATGCTCAATGACCGCCGCCGCCTGGCCCTGGAGAAC  1200
Sbjct 1286  ...............T....................................C.....T  1345

Query 1201  TACATCACCGCTCTGCAGGCTGTTCCTCCTCGGCCTCGTCACGTGTTCAATATGCTAAAG  1260
Sbjct 1346  ........T..A........G..G..C..AA......A..T........C.....G...  1405

Query 1261  AAGTATGTCCGCGCAGAACAGAAGGACAGACAGCACACCCTAAAGCATTTCGAGCATGTG  1320
Sbjct 1406  .....C.....T..G..G.....A........................T..A......  1465

Query 1321  CGCATGGTGGATCCCAAGAAAGCCGCTCAGATCCGGTCCCAGGTTATGACACACCTCCGT  1380
Sbjct 1466  ..........C.........T......................................  1525

Query 1381  GTGATTTATGAGCGCATGAATCAGTCTCTCTCCCTGCTCTACAACGTGCCTGCAGTGGCC  1440
Sbjct 1526  .....C..C........C........G............T..C.....G.....T  1585

Query 1441  GAGGAGATTCAGGATGAAGTTGATGAGCTGCTTCAGAAAGAGCAAAACTATTCAGATGAC  1500
Sbjct 1586  ............................................................  1645

Query 1501  GTCTTGGCCAACATGATTAGTGAACCAAGGATCAGTTACGGAAACGATGCTCTCATGCCA  1560
Sbjct 1646  ..............C.....G..C..A.....C..........G..A..........  1705

Query 1561  TCTTTGACCGAAACGAAAACCACCGTGGAGCTCCTTCCCGTGAATGGAGAGTTCAGCCTG  1620
Sbjct 1706  ..GC....G.....C..G..................................G..A..  1765

Query 1621  GACGATCTCCAGCCGTGGCATTCTTTTGGGGCTGACTCTGTGCCAGCCAACACAGAAAAC  1680
Sbjct 1766  ..T..C...........CC........TG................T..C.....T  1825

Query 1681  GAAGTTGAGCCTGTTGATGCCCGCCCTGCTGCCGACCGAGGACTGACCACTCGACCAGGT  1740
Sbjct 1826  .....C...........C........C.....T..........................  1885
```

Sequence Appendix

```
Query  1741  TCTGGGTTGACAAATATCAAGACGGAGGAGATCTCTGAAGTGAAGATGGATGCAGAATTC  1800
Sbjct  1886  ......C.......C.........A.........G........................  1945

Query  1801  CGACATGACTCAGGATATGAAGTTCATCATCAAAAA                          1836
Sbjct  1946  G.......T.......T......C.GC........                          1981

SEQ ID NO: 10
Score = 860 bits (434), Expect = 0.0
Identities = 719/814 (88%), Gaps = 0/814 (0%)
Strand = Plus/Plus Query    1  ATGCTGCCCGGTTTGGCACTGCTCCTGCTGGCCGCCTGGACGGCTCGGGCGCTGGAGGTA    60
Sbjct  146  .........A.C....................................T........T......  205

Query   61  CCCACTGATGGTAATGCTGGCCTGCTGGCTGAACCCCAGATTGCCATGTTCTGTGGCAGA   120
Sbjct  206  ...........C..C..C..G........A.........C...............T.A.  265

Query  121  CTGAACATGCACATGAATGTCCAGAATGGGAAGTGGGATTCAGATCCATCAGGGACCAAA   180
Sbjct  266  ..C...........G........A.........G.....C..G................  325

Query  181  ACCTGCATTGATACCAAGGAAGGCATCCTGCAGTATTGCCAAGAAGTCTACCCTGAACTG   240
Sbjct  326  ..........GC........G......T........C........G.............  385

Query  241  CAGATCACCAATGTGGTAGAAGCCAACCAACCAGTGACCATCCAGAACTGGTGCAAGCGG   300
Sbjct  386  ........A..C.....G.......G..................................  445

Query  301  GGCCGCAAGCAGTGCAAGACCCATCCCCACTTTGTGATTCCCTACCGCTGCTTAGTTGGT   360
Sbjct  446  ..................A..CA.....A.C........T.....T...C........  505

Query  361  GAGTTTGTAAGTGATGCCCTTCTCGTTCCTGACAAGTGCAAATTCTTACACCAGGAGAGG   420
Sbjct  506  ........G..C..C...........G..C............G...C...........C..  565

Query  421  ATGGATGTTTGCGAAACTCATCTTCACTGGCACACCGTCGCCAAAGAGACATGCAGTGAG   480
Sbjct  566  ...........T..G..C.....................................C....  625

Query  481  AAGAGTACCAACTTGCATGACTACGGCATGTTGCTGCCCTGCGGAATTGACAAGTTCCGA   540
Sbjct  626  .....C..T........C.....T.......C.............C..C.........  685

Query  541  GGGGTAGAGTTTGTGTGTTGCCCACTGGCTGAAGAAAGTGACAATGTGGATTCTGCTGAT   600
Sbjct  686  ...............A..C.....GT....C..G.....C....GC............G...  745

Query  601  GCGGAGGAGGATGACTCGGATGTCTGGTGGGGCGGAGCAGACACAGACTATGCAGATGGG   660
Sbjct  746  ..A..............T.............T......G...........C..T.....C  805

Query  661  AGTGAAGACAAAGTAGTAGAAGTAGCAGAGGAGGAAGAAGTGGCTGAGGTGGAAGAAGAA   720
Sbjct  806  G........................C..C..A.....G............T..T..G.....G  865

Query  721  GAAGCCGATGATGACGAGGACGATGAGGATGGTGATGAGGTAGAGGAAGAGGCTGAGGAA   780
Sbjct  866  .....T........T.....T.TG.........G..C.....G.....G.....C.....G  925

Query  781  CCCTACGAAGAAGCCACAGAGAGAACCACCAGCA                             814
Sbjct  926  ...........G.....C........A.......                             959

SEQ ID NO: 11
RAT
gi|27436860|ref|NM_019288.1|Rattus norvegicus (NORWEGIAN RAT) amyloid beta
(A4) precursor protein (App), mRNA
Length = 2341
Score = 1675 bits (871), Expect = 0.0
Identities = 1105/1222 (90%), Gaps = 0/1222 (0%)
Strand = Plus/Plus Query  866  TTCCTACAACAGCAGCCAGTACCCCTGATGCCGTTGACAAGTATCTCGAGACACCTGGGG   925
Sbjct 1116  ....C..G..G........C........C..A..C........C..G.....C..C..A.  1175

Query  926  ATGAGAATGAACATGCCCATTTCCAGAAAGCCAAAGAGAGGCTTGAGGCCAAGCACCGAG   985
Sbjct 1176  .......C..G..C.................................T.G..A......  1235

Query  986  AGAGAATGTCCCAGGTCATGAGAGAATGGGAAGAGGCAGAACGTCAAGCAAAGAACTTGC  1045
Sbjct 1236  .............................G..................C.....T....  1295

Query 1046  CTAAAGCTGATAAGAAGGCAGTTATCCAGCATTTCCAGGAGAAAGTGGAATCTTTGGAAC  1105
Sbjct 1296  .C........C........C.........................................C......  1355

Query 1106  AGGAAGCAGCCAACGAGAGACAGCAGCTGGTGGAGACACACATGGCCAGAGTGGAAGCCA  1165
Sbjct 1356  ....................G........T..A....................T.......  1415
```

-continued

Sequence Appendix

```
Query  1166  TGCTCAATGACCGCCGCCGCCTGGCCCTGGAGAACTACATCACCGCTCTGCAGGCTGTTC  1225
Sbjct  1416  .........T.....T...........C.....T...........A.......G..G.  1475

Query  1226  CTCCTCGGCCTCGTCACGTGTTCAATATGCTAAAGAAGTATGTCCGCGCAGAACAGAAGG  1285
Sbjct  1476  ....AA......A...T........C.....G........C.....T.....G......  1535

Query  1286  ACAGACAGCACACCCTAAAGCATTTCGAGCATGTGCGCATGGTGGATCCCAAGAAAGCCG  1345
Sbjct  1536  ..................T..A..........C.......T.  1595

Query  1346  CTCAGATCCGGTCCCAGGTTATGACACACCTCCGTGTGATTTATGAGCGCATGAATCAGT  1405
Sbjct  1596  .........................C..C...........C....  1655

Query  1406  CTCTCTCCCTGCTCTACAACGTGCCTGCAGTGGCCGAGGAGATTCAGGATGAAGTTGATG  1465
Sbjct  1656  .....G.................C.....C.....T...........A...........C.  1715

Query  1466  AGCTGCTTCAGAAAGAGCAAAACTATTCAGATGACGTCTTGGCCAACATGATTAGTGAAC  1525
Sbjct  1716  ..........G.....G.....C..C..C.........A...........C......  1775

Query  1526  CAAGGATCAGTTACGGAAACGATGCTCTCATGCCATCTTTGACCGAAACGAAAACCACCG  1585
Sbjct  1776  .C..A..........C........T........T.........G.....T.  1835

Query  1586  TGGAGCTCCTTCCCGTGAATGGAGAGTTCAGCCTGGACGATCTCCAGCCGTGGCATTCTT  1645
Sbjct  1836  .................C..A........T.........A..........C...  1895

Query  1646  TTGGGGCTGACTCTGTGCCAGCCAACACAGAAAACGAAGTTGAGCCTGTTGATGCCCGCC  1705
Sbjct  1896  ......TG.................T.........T.................C..C......  1955

Query  1706  CTGCTGCCGACCGAGGACTGACCACTCGACCAGGTTCTGGGTTGACAAATATCAAGACGG  1765
Sbjct  1956  .C.....T.................G........C.......A.  2015

Query  1766  AGGAGATCTCTGAAGTGAAGATGGATGCAGAATTCCGACATGACTCAGGATATGAAGTTC  1825
Sbjct  2016  .A........A...................G..G...G.......T.....C.TC.....C.  2075

Query  1826  ATCATCAAAAATTGGTGTTCTTTGCAGAAGATGTGGGTTCAAACAAAGGTGCAATCATTG  1885
Sbjct  2076  GC........C................................C......  2135

Query  1886  GACTCATGGTGGGCGGTGTTGTCATAGCGACAGTGATCGTCATCACCTTGGTGATGCTGA  1945
Sbjct  2136  .............T..C.........A........T.................  2195

Query  1946  AGAAGAAACAGTACACATCCATTCATCATGGTGTGGTGGAGGTTGACGCCGCTGTCACCG  2005
Sbjct  2196  .................C........C...........T....G....  2255

Query  2006  CAGAGGAGCGCCACCTGTCCAAGATGCAGCAGAACGGCTACGAAAATCCAACCTACAAGT  2065
Sbjct  2256  .G..............C................T...A..T..G.......A.......  2315

Query  2066  TCTTTGAGCAGATGCAGAACTA                                        2087
Sbjct  2316  ......................                                        2337
```

SEQ ID NO: 12
Score = 983 bits (511), Expect = 0.0
Identities = 715/817 (87%), Gaps = 0/817 (0%)
Strand = Plus/Plus

```
Query    1  ATGCTGCCCGGTTTGGCACTGCTCCTGCTGGCCGCCTGGACGGCTCGGGCGCTGGAGGTA   60
Sbjct   26  .........A.CC....................T......T........G   85

Query   61  CCCACTGATGGTAATGCTGGCCTGCTGGCTGAACCCCAGATTGCCATGTTCTGTGGCAGA  120
Sbjct   86  ...........C.....C..T........A...........C...............T.A.  145

Query  121  CTGAACATGCACATGAATGTCCAGAATGGGAAGTGGGATTCAGATCCATCAGGGACCAAA  180
Sbjct  146  ..C................G........A..A....G.....C.................  205

Query  181  ACCTGCATTGATACCAAGGAAGGCATCCTGCAGTATTGCCAAGAAGTCTACCCTGAACTG  240
Sbjct  206  ..........GC........G..A..........C........G................  265

Query  241  CAGATCACCAATGTGGTAGAAGCCAACCAACCAGTGACCATCCAGAACTGGTGCAAGCGG  300
Sbjct  266  ........A..C.....G.......G.........................  325

Query  301  GGCCGCAAGCAGTGCAAGACCCATCCCCACTTTGTGATTCCCTACCGCTGCTTAGTTGGT  360
Sbjct  326  ...................G..CA.....A.C........T.......G...C.....  385

Query  361  GAGTTTGTAAGTGATGCCCTTCTCGTTCCTGACAAGTGCAAATTCTTACACCAGGAGAGG  420
Sbjct  386  ..........C.........G..C..........G..TC..........C..  445

Query  421  ATGGATGTTTGCGAAACTCATCTTCACTGGCACACCGTCGCCAAAGAGACATGCAGTGAG  480
Sbjct  446  .....C.....T..G..C.............T..T..T....................  505
```

```
                            Sequence Appendix
Query  481  AAGAGTACCAACTTGCATGACTACGGCATGTTGCTGCCCTGCGGAATTGACAAGTTCCGA  540
Sbjct  506  .....C..T........C.....T......C...........T..C..C..........  565

Query  541  GGGGTAGAGTTTGTGTGTTGCCCACTGGCTGAAGAAAGTGACAATGTGGATTCTGCTGAT  600
Sbjct  566  .....C.....C.....C.....GT....G..G..G..C....GCA.C........G..C  625

Query  601  GCGGAGGAGGATGACTCGGATGTCTGGTGGGGCGGAGCAGACACAGACTATGCAGATGGG  660
Sbjct  526  ..A........C.....C.............T.....G...............T.....C  685

Query  661  AGTGAAGACAAAGTAGTAGAAGTAGCAGAGGAGGAAGAAGTGGCTGAGGTGGAAGAAGAA  720
Sbjct  686  G.............C..........C..A.....G........C..T..T..G......  745

Query  721  GAAGCCGATGATGACGAGGACGATGAGGATGGTGATGAGGTAGAGGAAGAGGCTGAGGAA  780
Sbjct  746  .....T..G..........T.TG........G........G.....G.....C.....G  805

Query  781  CCCTACGAAGAAGCCACAGAGAGAACCACCAGCATTG                         817
Sbjct  806  ...........G.................A.......                        842
```

Other Embodiments

All publications, patent applications, and patents mentioned in this specification are herein incorporated by reference.

Various modifications and variations of the described method and system of the invention will be apparent to those skilled in the art without departing from the scope and spirit of the invention. Although the invention has been described in connection with specific desired embodiments, it should be understood that the invention as claimed should not be unduly limited to such specific embodiments. Indeed, various modifications of the described modes for carrying out the invention that are obvious to those skilled in the fields of medicine, pharmacology, or related fields are intended to be within the scope of the invention.

What is claimed is:

1. A marrow-derived adult progenitor cell expressing recombinant sAPPα.

2. A pharmaceutical composition comprising marrow-derived adult progenitor cells (MAPCs) and a pharmaceutically acceptable excipient for intranasal administration, wherein said MAPCs express recombinant sAPPα.

3. The marrow-derived adult progenitor cell of claim 1, wherein said cell further expresses a trophic factor protein selected from the group consisting of TrkA, EGFR, IGFR, TrkB, Notch 1, Notch 2, Notch 3, Notch 4, BCHE, ChAT, Acetyl Coa, GSKb, CHRM 1, EGF, an FGF, IL3, VEGF, CDK1, CDK5RAP, FGF5, MYT2, a protein from the S100 family, a protein from the NTF family, a protein from the Notch family, SHH, a protein from the NEUROD family, a protein from the NEUROG family, a protein from the NHLH family, NRG1, BDNF, GDF11, GDNF, GPI, NRTN, a protein from the PDGF family, GFAP, GSS, and SOD1.

4. The marrow-derived adult progenitor cell of claim 1, wherein said cell further expresses a trophic factor protein selected from the group consisting of NGF, proNGF, IGF, LIF, CNTF, Sortilin, Int-2, Wnt, α-catenin, p75, NT-3, NT-4, FGF-1, PDGF, TGF, and TNF.

5. The pharmaceutical composition of claim 2, wherein the MAPCs further express a trophic factor protein selected from the group consisting of TrkA, EGFR, IGFR, TrkB, Notch 1, Notch 2, Notch 3, Notch 4, BCHE, ChAT, Acetyl Coa, GSKb, CHRM 1, EGF, an FGF, IL3, VEGF, CDK1, CDK5RAP, FGF5, MYT2, a protein from the S100 family, a protein from the NTF family, a protein from the Notch family, SHH, a protein from the NEUROD family, a protein from the NEUROG family, a protein from the NHLH family, NRG1, BDNF, GDF11, GDNF, GPI, NRTN, a protein from the PDGF family, GFAP, GSS, and SOD1.

6. The pharmaceutical composition of claim 2, wherein the MAPCs further express a trophic factor protein selected from the group consisting of NGF, proNGF, IGF, LIF, CNTF, Sortilin, Int-2, Wnt, α-catenin, p75, NT-3, NT-4, FGF-1, PDGF, TGF, and TNF.

* * * * *

UNITED STATES PATENT AND TRADEMARK OFFICE
CERTIFICATE OF CORRECTION

| | |
|---|---|
| PATENT NO. | : 8,168,169 B2 |
| APPLICATION NO. | : 11/891138 |
| DATED | : May 1, 2012 |
| INVENTOR(S) | : Anne Cataldo et al. |

It is certified that error appears in the above-identified patent and that said Letters Patent is hereby corrected as shown below:

On Title Page, under the Filing Date section, replace "Aug. 8, 2007" with --Aug. 9, 2007--.

Column 54, Claim 4, Line 41, replace "α-catenin" with --β-catenin--.

Column 54, Claim 6, Line 57, replace "α-catenin" with --β-catenin--.

Signed and Sealed this
Twenty-sixth Day of March, 2013

Teresa Stanek Rea
*Acting Director of the United States Patent and Trademark Office*

SEQUENCE LISTING

```
<160> NUMBER OF SEQ ID NOS: 12

<210> SEQ ID NO 1
<211> LENGTH: 2088
<212> TYPE: DNA
<213> ORGANISM: Homo sapien

<400> SEQUENCE: 1
atgctgcccg gtttggcact gctcctgctg gccgcctgga cggctcgggc gctggaggta    60
cccactgatg gtaatgctgg cctgctggct gaacccccaga ttgccatgtt ctgtggcaga   120
ctgaacatgc acatgaatgt ccagaatggg aagtgggatt cagatccatc agggaccaaa   180
acctgcattg ataccaagga aggcatcctg cagtattgcc aagaagtcta ccctgaactg   240
cagatcacca atgtggtaga agccaaccaa ccagtgacca tccagaactg gtgcaagcgg   300
ggccgcaagc agtgcaagac ccatccccac tttgtgattc cctaccgctg cttagttggt   360
gagtttgtaa gtgatgccct tctcgttcct gacaagtgca aattcttaca ccaggagagg   420
atggatgttt gcgaaactca tcttcactgg cacaccgtcg ccaaagagac atgcagtgag   480
aagagtacca acttgcatga ctacggcatg ttgctgccct gcggaattga caagttccga   540
ggggtagagt ttgtgtgttg cccactggct gaagaaagtg acaatgtgga ttctgctgat   600
gcggaggagg atgactcgga tgtctggtgg ggcggagcag acacagacta tgcagatggg   660
agtgaagaca aagtagtaga agtagcagag gaggaagaag tggctgaggt ggaagaagaa   720
gaagccgatg atgacgagga cgatgaggat ggtgatgagg tagaggaaga ggctgaggaa   780
ccctacgaag aagccacaga gagaaccacc agcattgcca ccaccaccac caccaccaca   840
gagtctgtgg aagaggtggt tcgagttcct acaacagcag ccagtaccccc tgatgccgtt   900 gacaagtatc tcgagacacc tggggatgag aatgaacatg cccatttcca gaagccaaa    960 gagaggcttg aggccaagca ccgagagaga atgtcccagg tcatgagaga atgggaagag  1020
```

```
gcagaacgtc aagcaaagaa cttgcctaaa gctgataaga aggcagttat ccagcatttc    1080
caggagaaag tggaatcttt ggaacaggaa gcagccaacg agagacagca gctggtggag    1140
acacacatgg ccagagtgga agccatgctc aatgaccgcc gccgcctggc cctggagaac    1200
tacatcaccg ctctgcaggc tgttcctcct cggcctcgtc acgtgttcaa tatgctaaag    1260
aagtatgtcc gcgcagaaca gaaggacaga cagcacaccc taaagcattt cgagcatgtg    1320
cgcatggtgg atcccaagaa agccgctcag atccggtccc aggttatgac acacctccgt    1380
gtgatttatg agcgcatgaa tcagtctctc tccctgctct acaacgtgcc tgcagtggcc    1440
gaggagattc aggatgaagt tgatgagctg cttcagaaag agcaaaacta ttcagatgac    1500
gtcttggcca acatgattag tgaaccaagg atcagttacg aaacgatgc tctcatgcca    1560 tctttgaccg aaacgaaaac caccgtggag ctccttcccg tgaatggaga gttcagcctg    1620
gacgatctcc agccgtggca ttcttttggg gctgactctg tgccagccaa cacagaaaac    1680
gaagttgagc ctgttgatgc ccgccctgct gccgaccgag gactgaccac tcgaccaggt    1740
tctgggttga caaatatcaa gacggaggag atctctgaag tgaagatgga tgcagaattc    1800
cgacatgact caggatatga agttcatcat caaaaattgg tgttctttgc agaagatgtg    1860
ggttcaaaca aggtgcaat cattggactc atggtgggcg tgttgtcat agcgacagtg    1920 atcgtcatca ccttggtgat gctgaagaag aaacagtaca catccattca tcatggtgtg    1980
gtggaggttg acgccgctgt cacccccagag gagcgccacc tgtccaagat gcagcagaac    2040
ggctacgaaa atccaaccta caagttcttt gagcagatgc agaactag                 2088

<210> SEQ ID NO 2
<211> LENGTH: 971
<212> TYPE: DNA
<213> ORGANISM: Pan troglodytes

<400> SEQUENCE: 2
ttcctacaac agcagccagt acccctgatg ccgttgacaa gtatctcgag acacctgggg     60
atgagaatga acatgcccat ttccagaaag ccaaagagag gcttgaggcc aagcaccgag    120
agagaatgtc ccaggtcatg agagaatggg aagaggcaga acgtcaagca aagaacttgc    180
ctaaagctga taagaaggca gttatccagc attccagga gaaagtggaa tctttggaac    240
aggaagcagc caacgagaga cagcagctgg tggagacaca catggccaga gtggaagcca    300
tgctcaatga ccgccgccgc ctggccctgg agaactacat caccgctctg caggctgttc    360
ctcctcggcc tcgtcacgtg ttcaatatgc taaagaagta tgtccgcgca gaacagaagg    420
acagacagca cacccctaaag catttcgagc atgtgcgcat ggtggatccc aagaaagctg    480
ctcagatccg gtcccaggtt atgacacacc tccgtgtgat ttacgagcgc atgaatcagt    540
ctctctccct gctctacaac gtgcctgcag tggccgagga gattcaggat gaagttgatg    600
agctgcttca gaaagagcaa aactattcag atgacgtctt ggccaacatg attagtgaac    660
caaggatcag ttacgaaaac gatgctctca tgccatcttt gaccgaaacg aaaaccaccg    720
tggagctcct tcccgtgaat ggagagttca gcctggacga tctccagccg tggcattctt    780
ttggggctga ctctgtgcca gccaacacag aaaacgaagt tgagcctgtt gatgcccgcc    840
ctgctgccga ccgaggactg accactcgac caggttctgg gttgacaaat atcaagacgg    900
aggagatctc tgaagtgaag atggatgcag aattccgaca tgactcagga tatgaagttc    960
atcatcaaaa a                                                         971
```

```
<210> SEQ ID NO 3
<211> LENGTH: 817
<212> TYPE: DNA
<213> ORGANISM: Homo sapien

<400> SEQUENCE: 3
atgctgcccg gtttggcgct gctcctgctg ccgcctgga cggctcgggc gctggaggta     60
cccactgatg gtaatgctgg cctgctggct gaaccccaga ttgccatgtt ctgtggcaga    120
ctgaacatgc acatgaatgt ccagaatggg aagtgggatt cagatccatc agggaccaaa    180
acctgcattg ataccaagga aggcatcctg cagtattgcc aagaagtcta ccctgaactg    240
cagatcacca atgtggtaga agccaaccaa ccagtgacca tccagaactg gtgcaagcgg    300
ggccgcaagc agtgcaagac ccatccccac tttgtgattc cctaccgctg cttagttggt    360
gagtttgtaa gtgatgccct tctcgttcct gacaagtgca aattcttaca ccaggagagg    420
atggatgttt gtgaaactca tcttcactgg cacaccgtcg ccaaagagac atgcagtgag    480
aagagtacca acttgcatga ctacggcatg ttgctgccct gcggaattga caagttccga    540
ggggtagagt ttgtgtgttg cccactggct gaagaaagtg acaatgtgga ttctgctgat    600
gcggaggagg atgactcgga tgtctggtgg ggcggagcag acacagacta tgcagatggg    660
agtgaagaca agtagtagaa agtagcagag gaggaagaag tggctgaggt ggaagaagaa    720
gaagccgatg atgacgagga cgatgaggat ggtgatgagg tagaggaaga ggctgaggaa    780
ccctacgaag aagccacaga gagaaccacc agcattg                             817

<210> SEQ ID NO 4
<211> LENGTH: 26
<212> TYPE: DNA
<213> ORGANISM: Homo sapien

<400> SEQUENCE: 4
agagtctgtg gaagaggtgg ttcgag                                          26

<210> SEQ ID NO 5
<211> LENGTH: 997
<212> TYPE: DNA
<213> ORGANISM: Pongo pygmaeus

<400> SEQUENCE: 5
agagtctgtg gaagaggtgg ttcgagttcc tacaacagca gccagtaccc ctgatgccgt     60
tgacaagtat ctcgagacac ctggggatga gaatgaacac gcccatttcc agaaagccaa    120
agagaggctt gaggccaagc accgagagag aatgtcccag gtcatgagag aatgggaaga    180
ggcagaacgt caagcaaaga acttgcctaa agctgataag aaggcagtta tccagcattt    240
ccaggagaaa gtggaatctt tggaacagga agcagccaac gagagacagc agctggtgga    300
gacacacatg gccagagtgg aagccatgct caatgaccgc cgccgcctgg ccctggagaa    360
ctacatcacc gctctgcagg ctgttcctcc tcggcctcgt cacgtgttca atatgctaaa    420
gaagtatgtc cgcgcagaac agaaggacag acagcacacc ctaaagcatt tcgagcatgt    480
gcgcatggtg gatcccaaga agctgctcaa gatccggtcc caggttatga cacacctccg    540
tgtgatttac gagcgcatga atcagtctct ctccctgctc tacaacgtgc ctgcagtggc    600
cgaggagatt caggatgaag ttgatgagct gcttcagaaa gagcaaaact attcagatga    660
cgtcttggcc aacatgatta gtgaaccaag gatcagttac ggaaacgaag ccctcatgcc    720
gtctttgacc gaaacgaaaa ccaccgtgga gcttcttcct gtgaatggag agttcagcct    780
ggacgatctc cagccgtggc attctttggg ggctgactct gtgccagcca acacagaaaa    840
```

```
cgaagttgag cctgttgatg cccgtcctgc tgccgaccgg ggactgacca ctcgaccagg    900
ttctgggttg acaaatatca agacggagga gatctctgaa gtgaagatgg atgcagaatt    960
ccgacatgac tcgggatatg aagttcatca tcaaaaa                             997

<210> SEQ ID NO 6
<211> LENGTH: 815
<212> TYPE: DNA
<213> ORGANISM: Pongo pygmaeus

<400> SEQUENCE: 6
atgctgcccg tttggcact gctcctgctg ccgcctgga cggctcgggc gctggaggta      60
cccactgatg gcaatgctgg cctgctggct gaaccccaga ttgccatgtt ctgtggcaga   120
ctgaacatgc acatgaatgt ccagaatggg aagtgggatt cagatccatc agggaccaaa   180
acctgcattg ataccaagga aggcatcctg cagtattgcc aagaagtcta ccctgaactg   240
cagatcacca atgtggtaga agccaaccaa ccagtgacca tccagaactg gtgcaagcgg   300
ggccgcaagc agtgcaagac ccatccccac tttgtgattc cctaccgctg cttagttggt   360
gaatttgtaa gcgatgccct ctcgttcct gacaagtgca aattcttgca ccaggagagg    420
atggatgttt gtgaaactca tcttcactgg cacaccgtcg ccaaagagac gtgcagtgag   480
aagagtacca acttgcatga ctacggcatg ttgctgccct gcggaattga caagttccga   540
ggggtagagt ttgtgtgttg cccactggct gaggaaagtg acaatgtgga ttctgctgac   600
gcggaggagg atgactcgga tgtctggtgg ggcggagcag acacagacta tgcagatggg   660
agtgaagaca agtagtaga agtagcagag gaggaagaag tggctgaggt ggaagaagaa   720
gaagctcatg atgacgagga tgatgaggat ggtgacgagg tagaggaaga ggctgaggaa   780
ccctacggag aagccacaga gagaaccacc agcat                              815

<210> SEQ ID NO 7
<211> LENGTH: 996
<212> TYPE: DNA
<213> ORGANISM: M.fascicularis

<400> SEQUENCE: 7
gagtctgtgg aagaggtggt tcgagttcct acaacagcag ccagtacccc tgatgccgtt    60
gacaagtacc ttgagacacc tgggggatgag aatgaacacg cccatttcca gaaagccaaa   120
gagagacttg aggccaagca ccgagagaga atgtcccagg tcatgagaga atgggaagag   180
gcagaacgtc aggcaaagaa cttgcctaaa gctgataaga aggcagttat ccagcatttc    240
caggagaaag tggaatcttt ggaacaggaa gcagccaacg agagacagca gctggtggag    300
acacacatgg ccagagtgga agccatgctc aatgaccgcc gccgcctggc cctggagaac    360
tacatcactg ctctgcaggc cgttcctcct cggcctcgtc acgtgttcaa tatgctgaag    420
aagtacgtcc gcgcagaaca gaaggacaga cagcacaccc tgaagcattt cgagcatgta    480
cgcatggtgg atcccaagaa agctgctcag atccggtccc aggttatgac acacctccgt   540
gtgatttacg agcgcatgaa tcagtccctc tccctgctct acaacgtgcc tgcagtggcc    600
gaggagattc aggatgaagt tgatgagctg cttcagaaag agcaaaacta ttcagatgac   660
gtcttggcca acatgattag tgaaccaagg atcagttacg aaacgatgc tctcatgccg   720 tctttgaccg aaacgaaaac taccgtggag cttcttcccg tgaatggaga gttcagcctg    780
gacgatctcc agccgtggca ttcttcggg gctgactctg tgccagccaa cacagaaaac   840
gaagttgagc ctgttgatgc ccgccctgct gccgaccgag gactgaccac tcgaccaggt    900
```

```
tctgggttga caaatatcaa gacagaggag atctctgaag tgaagatgga tgcagaattc    960
cgacatgact caggttatga agttcatcat caaaaa                              996
```

```
<210> SEQ ID NO 8
<211> LENGTH: 815
<212> TYPE: DNA
<213> ORGANISM: M.fascicularis

<400> SEQUENCE: 8
```

```
atgctgcccg gtttggcact gctcctgctg gccgcctgga cggctcgggc gctggaggta     60
cctactgatg gcaatgctgg cctgctggct gaaccccaga tcgccatgtt ctgtggcaga    120
ctgaacatgc acatgaatgt ccagaatggg aagtgggatt cagatccatc agggaccaaa    180
acctgcattg ataccaagga aggcatcctg cagtattgcc aagaagtcta ccctgaactg    240
cagatcacca atgtggtaga agccaaccaa ccagtgacca tccagaactg gtgcaagagg    300
ggccgcaagc agtgcaagac ccatccccac tttgtgattc cctaccgctg tttagttggt    360
gagtttgtaa gcgatgccct tctcgttcct gacaagtgca aattcttaca ccaggagagg    420
atggatgttt gcgaaactca tcttcactgg cacaccgtcg ccaaagagac gtgcagtgag    480
aagagcacca acttgcatga ctacggcatg ttgctgccct gtggaatcga taagttccga    540
ggggtagagt ttgtgtgttg cccactggct gaggaaagtg acaatgtgga ttctgctgat    600
gcggaggagg atgactcgga tgtctggtgg ggcggagcag acacagacta tgcagacggg    660
agtgaagaca aagtagtaga agtagcagag gaggaagaag tggccgaggt ggaagaagaa    720
gaagccgatg atgacgagga cgatgaggat ggtgatgagg tagaggaaga ggctgaggaa    780
ccctacgaag aagccacaga gagaaccacc agcat                               815
```

```
<210> SEQ ID NO 9
<211> LENGTH: 996
<212> TYPE: DNA
<213> ORGANISM: Mus musculus

<400> SEQUENCE: 9
```

```
gagtccgtgg aggaggtggt ccgagttccc acgacagcag ccagcacccc cgacgccgtc     60
gacaagtacc tggagacacc cggggacgag aacgagcatg cccatttcca gaaagccaaa    120
gagaggctgg aagccaagca ccgagagaga atgtcccagg tcatgagaga atgggaagag    180
gcagagcgtc aagccaagaa cttgcccaaa gctgacaaga aggccgttat ccagcatttc    240
caggagaaag tggaatctct ggaacaggaa gcagccaatg agagacagca gcttgtagag    300
acacacatgg ccagagttga agccatgctc aatgaccgcc gccgcctggc cctcgagaat    360
tacatcactg cactgcaggc ggtgcccccca aggcctcatc atgtgttcaa catgctgaag    420
aagtacgtcc gtgcggagca gaaagacaga cagcacaccc taaagcattt tgaacatgtg    480
cgcatggtgg accccaagaa agctgctcag atccggtccc aggttatgac acacctccgt    540
gtgatctacg agcgcatgaa ccagtctctg tccctgctct acaatgtccc tgcggtggct    600
gaggagattc aagatgaagt cgatgagctg cttcagaagg agcagaacta ctccgacgat    660
gtcttggcca acatgatcag tgagcccaga atcagctacg aaacgacgc tctcatgcct    720 tcgctgacgg aaaccaagac caccgtggag ctccttcccg tgaatgggga attcagcctg    780
gatgacctcc agccgtggca cccttttggg gtggactctg tgccagccaa taccgaaaat    840
gaagtcgagc ctgttgacgc ccgccccgct gctgaccgag actgaccac tcgaccaggt    900 tctgggctga caaacatcaa gacggaagag atctcggaag tgaagatgga tgcagaattc    960
```

| | |
|---|---|
| ggacatgatt caggatttga agtccgccat caaaaa | 996 |

<210> SEQ ID NO 10
<211> LENGTH: 814
<212> TYPE: DNA
<213> ORGANISM: Mus musculus

<400> SEQUENCE: 10

| | |
|---|---|
| atgctgccca gcttggcact gctcctgctg gccgcctgga cggttcgggc tctggaggta | 60 |
| cccactgatg gcaacgccgg gctgctggca gaaccccaga tcgccatgtt ctgtggtaaa | 120 |
| ctcaacatgc acatgaatgt gcagaatgga aagtgggagt cagacccgtc agggaccaaa | 180 |
| acctgcattg gcaccaagga gggcatcttg cagtactgcc aagaggtcta ccctgaactg | 240 |
| cagatcacaa cgtggtgga agccaaccag ccagtgacca tccagaactg gtgcaagcgg | 300 |
| ggccgcaagc agtgcaagac acacacccac atcgtgattc cttaccgttg cctagttggt | 360 |
| gagtttgtga gcgacgccct tctcgtgccc gacaagtgca agttcctaca ccaggagcgg | 420 |
| atggatgttt gtgagaccca tcttcactgg cacaccgtcg ccaaagagac atgcagcgag | 480 |
| aagagcacta acttgcacga ctatggcatg ctgctgccct gcggcatcga caagttccga | 540 |
| ggggtagagt ttgtatgctg cccgttggcc gaggaaagcg acagcgtgga ttctgcggat | 600 |
| gcagaggagg atgactctga tgtctggtgg ggtggagcgg acacagacta cgctgatggc | 660 |
| ggtgaagaca agtagtaga agtcgccgaa gaggaggaag tggctgatgt tgaggaagag | 720 |
| gaagctgatg atgatgagga tgtggaggat ggggacgagg tggaggagga ggccgaggag | 780 |
| ccctacgaag aggccaccga gagaacaacc agca | 814 |

<210> SEQ ID NO 11
<211> LENGTH: 1222
<212> TYPE: DNA
<213> ORGANISM: Rattus norvegicus

<400> SEQUENCE: 11

| | |
|---|---|
| ttcccacgac ggcagccagc acccctgacg cagtcgacaa gtacctggag accccccggag | 60 |
| atgagaacga gcacgcccat ttccagaaag ccaaagagag gttggaagcc aagcaccgag | 120 |
| agagaatgtc ccaggtcatg agagaatggg aggaggcaga acgtcaagcc aagaatttgc | 180 |
| ccaaagctga caagaaggcc gttatccagc atttccagga gaaagtggaa tctctggaac | 240 |
| aggaagcagc caacgagagg cagcagcttg tagagacaca catggccaga gttgaagcca | 300 |
| tgctcaatga tcgccgtcgc ctggccctcg agaattacat caccgcactg caggcggtgc | 360 |
| ctccaaggcc tcatcatgtg ttcaacatgc tgaagaagta cgtccgtgca gagcagaagg | 420 |
| acagacagca caccctaaag cattttgaac atgtgcgcat ggtggacccc aagaaagctg | 480 |
| ctcagatccg gtcccaggtt atgacacacc tccgtgtgat ctacgagcgc atgaaccagt | 540 |
| ctctgtccct gctctacaac gtccctgccg tggctgagga gattcaagat gaagttgacg | 600 |
| agctgcttca gaaggagcag aactactccg acgacgtctt agccaacatg atcagtgaac | 660 |
| ccagaatcag ttacggcaac gatgctctca tgccttcttt gactgaaacg aagaccactg | 720 |
| tggagctcct tcccgtgaat ggcgaattca gcctggatga tctccaaccg tggcatcctt | 780 |
| ttgggggtgga ctctgtgcca gccaatacag aaaatgaagt tgagcctgtc gacgcccgcc | 840 |
| ccgctgctga ccgagggctg accactcgac caggttctgg gttgacaaac atcaagacag | 900 |
| aagagatctc agaagtgaag atggatgcgg agttcggaca tgattcaggc ttcgaagtcc | 960 |
| gccatcaaaa actggtgttc tttgcagaag atgtgggttc aaacaaaggt gccatcattg | 1020 |

```
                                      -continued gactcatggt gggtggcgtt gtcatagcaa cagtgattgt catcaccttg gtgatgctga    1080
agaagaaaca gtacacatcc atccatcatg gcgtggtgga ggttgacgct gctgtgaccc    1140
cggaggagcg ccacctctcc aagatgcagc agaatggata tgagaatcca acatacaagt    1200
tctttgagca gatgcagaac ta                                             1222

<210> SEQ ID NO 12
<211> LENGTH: 818
<212> TYPE: DNA
<213> ORGANISM: Rattus norvegicus

<400> SEQUENCE: 12
atgctgccca gcctggcact gctcctgctg gccgcctgga cggttcgggc tctggaggtg      60
cccactgatg gcaatgccgg tctgctggca gaacccagag tcgccatgtt ctgtggtaaa     120
ctcaacatgc acatgaatgt gcagaatgga aaatgggagt cagacccatc agggaccaaa    180
acctgcattg agcaccaagg agggaatcct gcagtactgc caagaggtct accctgaact     240
gcagatcaca aacgtggtgg aagccaacca gccagtgacc atccagaact ggtgcaagcg    300
gggccgcaag cagtgcaaga cgcacaccca catcgtgatt ccttaccggt gcctagttgg    360
tgagtttgta agcgatgccc ttctcgtgcc cgacaagtgc aagtttctac accaggagcg     420
gatggacgtt tgtgagaccc atcttcactg gcatactgtt gccaaagaga catgcagtga    480
gaagagcact aacttgcacg actatggcat gctgctgccc tgtggcatcg acaagttccg     540
aggggtcgag ttcgtgtgct gcccgttggc ggaggagagc gacagcatcg attctgcgga    600
cgcagaggag gacgactccg atgtctggtg gggtggagcg gacacagact atgctgatgg     660
cggtgaagac aaagtcgtag aagtagccga agaggaggaa gtggccgatg ttgaggaaga    720
agaagctgag gatgacgagg atgtggagga tgggatgag gtggaggagg aggccgagga    780
gccctacgaa gaggccacag agaacaac cagcattg                              818
```